United States Patent
Eggenweiler et al.

(12) United States Patent     (10) Patent No.: US 7,485,639 B2
(45) Date of Patent: Feb. 3, 2009

(54) 4-(BENZYLIDENE-AMINO)-3-(METHYL SULFANYL)-4H-(1,2,4)TRIAZIN-5-ONE DERIVATIVES HAVING A PDE-IV INHIBITING AND TNF-ANTAGONISTIC EFFECT FOR THE TREATMENT OF CARDIAC DISEASES AND ALLERGIES

(75) Inventors: Hans-Michael Eggenweiler, Darmstadt (DE); Michael Wolf, Darmstadt (DE); Norbert Beier, Reinheim (DE); Joachim Leibrock, Pfungstadt (DE); Pierre Schelling, Mühltal (DE); Michael Gassen, München (DE); Thomas Ehring, Remscheid (DE)

(73) Assignee: Merck Patent GmbH, Darmstadt (DE)

( * ) Notice: Subject to any disclaimer, the term of this patent is extended or adjusted under 35 U.S.C. 154(b) by 620 days.

(21) Appl. No.: 10/484,172

(22) PCT Filed: Jun. 19, 2002

(86) PCT No.: PCT/EP02/06742

§ 371 (c)(1),
(2), (4) Date: Jan. 20, 2004

(87) PCT Pub. No.: WO03/008392

PCT Pub. Date: Jan. 30, 2003

(65) Prior Publication Data

US 2004/0176252 A1    Sep. 9, 2004

(30) Foreign Application Priority Data

Jul. 18, 2001 (DE) ................ 101 35 009
Nov. 15, 2001 (DE) ................ 101 56 229

(51) Int. Cl.
*A01N 43/64* (2006.01)
*A61K 31/53* (2006.01)
*C07D 253/00* (2006.01)

(52) U.S. Cl. ................ 514/242; 544/182
(58) Field of Classification Search ........ 544/182, 544/242; 514/242
See application file for complete search history.

(56) References Cited

U.S. PATENT DOCUMENTS

| | | | |
|---|---|---|---|
| 4,036,632 A * | 7/1977 | Westphal et al. ............ 504/229 |
| 4,346,220 A | 8/1982 | Fawzi | |
| 5,859,008 A | 1/1999 | Jonas et al. | |
| 6,218,391 B1 | 4/2001 | Arvanitis et al. | |
| 6,290,929 B1 | 9/2001 | Camden | |

FOREIGN PATENT DOCUMENTS

| | | |
|---|---|---|
| EP | 0763534 | 3/1997 |
| FR | 1519180 | 3/1968 |
| FR | 1547854 | 11/1968 |
| WO | WO 98/11075 | * 3/1998 |
| WO | WO 9811075 | 3/1998 |
| WO | WO 0209715 | 2/2002 |

* cited by examiner

*Primary Examiner*—Alton N Pryor

(57) ABSTRACT

Triazine derivatives of the formula (I) and physiologically acceptable salts and solvates thereof, in which $R^1$, $R^2$, A and $R^5$ are as defined in Claim 1, exhibit phosphodiesterase IV inhibition and can be employed for the treatment of allergic diseases, asthma, chronic bronchitis, atopic dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS, furthermore for inhibiting the formation of TNFα.

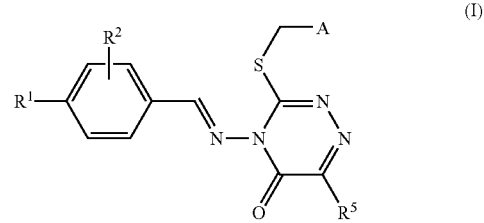

(I)

10 Claims, No Drawings

4-(BENZYLIDENE-AMINO)-3-(METHYL SULFANYL)-4H-(1,2,4)TRIAZIN-5-ONE DERIVATIVES HAVING A PDE-IV INHIBITING AND TNF-ANTAGONISTIC EFFECT FOR THE TREATMENT OF CARDIAC DISEASES AND ALLERGIES

The invention relates to compounds of the formula I

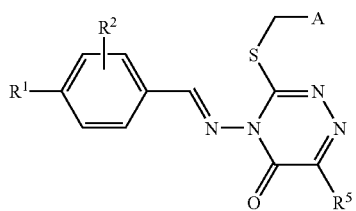

in which
$R^1$ and $R^2$ are each, independently of one another, H, OH, $OR^6$, $SR^6$, $SOR^6$, $SO_2R^6$, Hal or together are alternatively —O—$CH_2$—O—,
A is $R^3$- and $R^4$-substituted phenyl, 2-, 3- or 4-pyridyl, 4- or 5-pyrimidyl, 3- or 4-pyridazyl or 2- or 3-pyrazinyl,
$R^3$ and $R^4$ are each, independently of one another, H, OH, $OR^6$, $SR^6$, $SOR^6$, $SO_2R^6$, $R^6$, Hal or together are alternatively —O—$CH_2$—O—,
$R^5$ is H or alkyl having from 1 to 10 carbon atoms,
$R^6$ is alkyl having from 1 to 10 carbon atoms, which may be substituted by from 1 to 5 F and/or Cl atoms, cycloalkyl having 3-7 carbon atoms, alkylenecycloalkyl having 5-10 carbon atoms or alkenyl having 2-8 carbon atoms,
Hal is F, Cl, Br or I, and physiologically acceptable salts and solvates thereof.

Similar compounds are already known (for example CAS Reg. No. 292057-55-7). However, the compounds according to the invention differ from the known compounds in the nature and position of the substituents.

The invention had the object of finding novel compounds having valuable properties, in particular those which can be used for the preparation of medicaments.

It has been found that the compounds of the formula I and salts and solvates thereof have very valuable pharmacological properties and are well tolerated.

In particular, they exhibit selective phosphodiesterase IV inhibition combined with an intracellular increase in cAMP (N. Sommer et al., Nature Medicine, 1, 244-248 (1995)).

The PDE IV inhibition can be demonstrated, for example, analogously to C. W. Davis in Biochim. biophys. Acta 797, 354-362 (1984).

The compounds according to the invention can be employed for the treatment of asthmatic diseases. The antiasthmatic action of PDE IV inhibitors has been described, for example, by T. J. Torphy et al. in Thorax, 46, 512-523 (1991) and can be determined, for example, by the method of T. Olsson, Acta allergologica 26, 438-447 (1971).

Since cAMP inhibits bone-degrading cells and stimulates bone-forming cells (S. Kasugai et al., M 681 and K. Miyamoto, M 682, in Abstracts of the American Society for Bone and Mineral Research 18th Annual Meeting, 1996), the compounds according to the invention can be employed for the treatment of osteoporosis.

The invention therefore furthermore relates to the use of the compounds of the formula I and/or physiologically acceptable salts and solvates thereof for the preparation of a medicament for the treatment and prophylaxis of diseases which are caused by an excessively low cAMP level and/or can be influenced by an increase in the cAMP level.

In addition, the compounds exhibit an antagonistic action to the production of TNFα (tumour necrosis factor) and are therefore suitable for the treatment of allergic and inflammatory diseases, autoimmune diseases, such as, for example, rheumatoid arthritis, multiple sclerosis, Crohn's disease, diabetes mellitus or ulcerative colitis, transplant rejection reactions, cachexia and sepsis.

The antiinflammatory action of the substances according to the invention and the efficacy thereof for the treatment of, for example, autoimmune diseases, such as multiple sclerosis or rheumatoid arthritis, can be determined analogously to the methods of N. Sommer et al., Nature Medicine 1, 244-248 (1995) or L. Sekut et al., Clin. Exp. Immunol. 100, 126-132 (1995).

The compounds can be employed for the treatment of cachexia. The anticachectic action can be tested in TNF-dependent models of cachexia (P. Costelli et al., J. Clin. Invest. 95, 2367ff. (1995); J. M. Argiles et al., Med. Res. Rev. 17, 477ff. (1997)).

PDE IV inhibitors can also inhibit the growth of tumour cells and are therefore suitable for tumour therapy (D. Marko et al., Cell Biochem. Biophys. 28, 75ff. (1998)). The action of PDE IV inhibitors in the treatment of tumours is described, for example, in WO 95 35 281, WO 95 17 399 or WO 96 00 215.

The invention therefore furthermore relates to the use of the compounds of the formula I and/or physiologically acceptable salts and solvates thereof for the preparation of a medicament for the treatment and prophylaxis of diseases which are caused by excessive production of tumour necrosis factor (TNF) and/or can be influenced by a reduction in the production of TNF.

PDE IV inhibitors can prevent mortality in models for sepsis and are therefore suitable for the therapy of sepsis (W. Fischer et al., Biochem. Pharmacol. 45, 2399ff. (1993)).

They can furthermore be employed for the treatment of memory disorders, atherosclerosis, atopic dermatitis and AIDS.

The action of PDE IV inhibitors in the treatment of asthma, inflammatory diseases, diabetes mellitus, atopic dermatitis, psoriasis, AIDS, cachexia, tumour growth or tumour metastases is described, for example, in EP 779291.

The compounds of the formula I have broad potential therapeutic applications as inhibitors of PDE IV isozymes since the PDE IV family of isozymes plays a crucial role in the physiology of all mammals. PDE IV isozymes effect intracellular hydrolysis of adenosine 3',5'-monophosphates (cAMP) in pro-inflammatory leukocytes. cAMP is in turn responsible for mediation of the action of numerous hormones in the body.

There is a vast literature which describes the effects of PDE inhibitors on a wide variety of inflammatory cell responses, which, in addition to increasing the cAMP level, also include inhibition of superoxide production, degranulation, chemotaxis and liberation of tumour necrosis factor (TNF) in eosinophiles, neutrophiles and monocytes.

The invention therefore furthermore relates to the use of the compounds of the formula I and/or physiologically tolerated salts and/or solvates thereof for the preparation of a medicament for the treatment or prophylaxis of diseases which are caused by disorders in the regulation of the activation and degranulation of human eosinophiles.

The compounds of the formula I can be employed as medicament active ingredients in human and veterinary medicine. They can furthermore be employed as intermediates for the preparation of further medicament active ingredients.

The compounds of the formula I can preferably also be used together with one or more known PDE IV inhibitors. The compounds of the formula I are preferably used together with one or more of the PDE IV inhibitors published in the following documents: EP 0763534, WO 99/65880, WO 99/08047, WO 98/06704, WO 00/59890, DE 19604388, DE 19932315, EP 0723962, EP 0738715.

The invention also relates to the use of the compounds of the formula I as PDE IV inhibitors for the treatment of myocardial diseases.

Coronary heart disease is the most frequent cause of death in western countries. If a coronary artery is critically narrowed, the reduced blood flow can result in myocardial ischaemia. Depending on the severity of the prior ischaemic period, commencement of reperfusion results in reversible or irreversible myocardial damage which is characterised by long-lasting depression or an irreversible loss of contractile function. Depending on the size of the affected myocardial area, acute or chronic heart failure can occur.

A particular clinical problem in the above-described scenario is the onset of restenosis after an initially successful reperfusion intervention by PTCA (percutaneous transluminal coronary angioplasty), even after stent implantation, thrombolysis or the insertion of an aorto-coronary bypass. Animal experiment and clinical studies indicate that inflammatory processes play a causative role in the various above-mentioned heart diseases, for example in coronary heart disease itself, in reversible or irreversible myocardial ischaemia/reperfusion damage, in acute or chronic heart failure and in restenosis, including in-stent restenosis and stent-in-stent restenosis. Resident and invading macrophages as well as neutrophilic cells and TH1 and TH2 helper cells are involved in these inflammatory processes. This leukocyte reaction results in a characteristic cytokine pattern involving TNF-$\alpha$, IL-1$\beta$, IL-2 and IL-6 as well as IL-10 and IL-13 (Pulkki K J: Cytokines and cardiomyocyte death, Ann. Med. 1997 29: 339-343. Birks E J, Yacoub M H: The role of nitric oxide and cytokines in heart failure. Coron. Artery. Dis. 1997 8: 389-402).

It has been found that these species are formed in human patients with myocardial ischaemia. Animal models show that cytokine production correlates with invasion by peripheral macrophages and neutrophilic cells, which can spread the damage into the still intact myocardium. However, the main role in the cytokine reaction is played by TNF-$\alpha$, which integrates inflammatory and pro-apoptotic reactions and in addition has a direct negative ionotropic effect on myocardial cells (Ceconi C, Curello S, Bachetti T, Corti A, Ferrari R: Tumor necrosis factor in congestive heart failure: a mechanism of disease for the new millennium? Pro. Cardiovas. Dis. 1998 41: 25-30. Mann D L: The effect of tumor necrosis factor-alpha on cardiac structure and function: a tale of two cytokines. J. Card. Fail. 1996 2: S165-S175. Squadrito F, Altavilla D, Zingarelli B, et al.: Tumor necrosis factor involvement in myocardial ischaemia-reperfusion injury. Eur. J. Pharmacol. 1993 237: 223-230).

Animal models of cardiac infarction have shown that rapid release of TNF$\alpha$ occurs during the reperfusion phase (Herskowitz A, Choi S, Ansari A A, Wesselingh S: Cytokine mRNA expression in postischemic/reperfused myocardium. Am. J. Pathol. 1995 146: 419-428) and that the protective action of medicaments, such as dexamethason (Arras M, Strasser R, Mohri M, et al.: Tumor necrosis factor-alpha is expressed by monocytes/macrophages following cardiac microembolization and is antagonized by cyclosporine, Basic. Res. Cardiol. 1998 93:97-107), cyclosporin A (Arras M, Strasser R, Mohri M, et al.: Tumor necrosis factor-alpha is expressed by monocytes/macrophages following cardiac microembolization and is antagonized by cyclosporine, Basic. Res. Cardiol. 1998 93:97-107, Squadrito F, Altavilla D, Squadrito G, et al.: Cyclosporin-A reduces leukocyte accumulation and protects against myocardial ischaemia reperfusion injury in rats. Eur. J. Pharmacol. 1999 364: 159-168) or clorichromene (Squadrito F, Altavilla D, Zingarelli B, et al.: The effect of cloricromene, a coumarine derivative, on leukocyte accumulation, myocardial necrosis and TNF-alpha production in myocardial ischaemia-reperfusion injury. Life Sci. 1993 53: 341-355), is associated with a reduction in the TNF-$\alpha$ in circulation.

The present invention therefore also relates to the use of the compounds of the formula I and/or physiologically acceptable salts and solvates thereof for the preparation of a medicament for the treatment and prophylaxis of diseases which can be influenced by a reduction in the production of tumour necrosis factor (TNF).

The PDE IV inhibitors of the formula I are potential antagonists of the production of macrophages and T-cell cytokines. In addition, they inhibit the proliferation of T-cells. As a consequence, PDE IV inhibition can have an advantageous effect in myocardial diseases in which there is a causal link to the production of cytokines and inflammatory processes.

The use of the compounds of the formula I and/or physiologically acceptable salts and solvates thereof for the preparation of a medicament for the treatment and prophylaxis of diseases which is caused by excessive production of macrophages and T-cells and/or can be influenced by a reduction in macrophage and T-cell production is likewise a subject-matter of the present invention.

The present invention furthermore relates to the use of the compounds of the formula I and/or physiologically acceptable salts and solvates thereof for the preparation of a medicament for the treatment and prophylaxis of diseases which are caused by excessive proliferation of T-cells and/or can be influenced by inhibition of the proliferation of T-cells.

Compared with PDE III inhibitors and the early PDE IV inhibitor rolipram, preferred PDE IV inhibitors of the formula I do not exhibit any haemodynamic side effects which could have a dose-limiting effect in the treatment of most cardiovascular diseases.

The invention has the object of finding novel uses for compounds having valuable properties, in particular those which are suitable for the preparation of medicaments.

It has been found that the PDE IV inhibitors of the formula I and salts and solvates thereof exhibit very valuable pharmacological properties in the treatment of myocardial diseases and at the same time are well tolerated.

The preferred compounds effect selective inhibition of phosphodiesterase IV, which is associated with an intracellular increase in the cAMP concentration (N. Sommer et al., Nature Medicine, 1, 244-248 (1995)). Inhibition of PDE IV can be demonstrated, for example, as described by C. W. Davis, Biochim. Biophys. Acta 797, 354-362 (1984).

The affinity of the compounds according to the invention for phosphodiesterase IV is measured by determining their $IC_{50}$ values (the inhibitor concentration necessary to inhibit the enzyme activity by 50%).

The present application therefore furthermore relates to the use of the compounds of the formula and/or physiologically acceptable salts and solvates thereof for the preparation of a medicament for the treatment and prophylaxis of diseases which can be influenced by an increase in the cAMP level.

The invention preferably provides the use of the abovementioned compounds for the preparation of a medicament for the treatment of myocardial diseases which have inflammatory and immunological characteristics.

The invention very particularly preferably provides the use of the abovementioned compounds for the preparation of a medicament for the treatment of coronary heart disease, reversible or irreversible myocardial ischaemia/reperfusion damage, acute or chronic heart failure, decompensated cardiac insufficiency (congestive heart failure, CHF) and restenosis, including in-stent restenosis and stent-in-stent restenosis.

The compounds of the formula and/or salts and/or solvates thereof are furthermore suitable for the preparation of a medicament for the prophylaxis and treatment of ventricular remodelling after infarction or decompensated cardiac insufficiency (congestive heart failure, CHF) of varying severity.

The preparations for the treatment of the diseases mentioned can be employed as medicaments in human and veterinary medicine. Possible excipients are organic or inorganic substances which are suitable for enteral (for example oral) or parenteral administration or topical application and which do not react with the novel compounds, for example water, vegetable oils, benzyl alcohols, alkylene glycols, polyethylene glycols, glycerol triacetate, gelatine, carbohydrates, such as lactose or starch, magnesium stearate, talc and Vaseline. In particular, tablets, pills, coated tablets, capsules, powders, granules, syrups, juices or drops are employed for oral administration, suppositories for rectal administration, solutions, preferably oil-based or aqueous solutions, and furthermore suspensions, emulsions or implants for parenteral administration, and ointments, creams or powders for topical application. It is also possible to lyophilise the novel compounds and to use the resultant lyophilisates, for example, for the preparation of injection preparations. The preparations indicated may be sterilised and/or comprise adjuvants, such as, for example, lubricants, preservatives, stabilisers and/or wetting agents, emulsifiers, salts for modifying the osmotic pressure, buffers, dyes, flavours and/or one or more further active ingredients, for example one or more vitamins.

In these indications, the substances are generally preferably administered in doses of from about 1 to 500 mg, in particular from 5 to 100 mg, per dosage unit. The daily dose is preferably from about 0.02 to 10 mg/kg of body weight. However, the specific dose for the particular patient depends on a number of factors, for example on the efficacy of the compound used, on the age, body weight, general state of health, sex, on the diet, on the time and method of administration, on the excretion rate, the medicament combination and the severity of the disease against which the therapy is employed. Oral administration is preferred.

The invention accordingly relates to the compounds of the formula I and to a process for the preparation of compounds of the formula I according to claim 1 and salts and solvates thereof, characterised in that a compound of the formula II

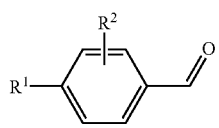

in which
$R^1$ and $R^2$ are as defined,
is reacted with a compound of the formula III

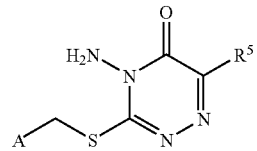

III in which
A and $R^5$ are as defined above, and/or in that a basic compound of the formula I is converted into one of its salts by treatment with an acid.

The novel compounds of the formula III are likewise a subject-matter of the invention.

The term "solvates of the compounds of the formula I" is taken to mean adductions of preferably inert solvent molecules onto the compounds of the formula I which form owing to their mutual attractive force. Solvates are, for example, monohydrates or dihydrates or alcoholates.

Above and below, the radicals $R^1$, $R^2$, A, $R^3$, $R^4$, $R^5$ and $R^6$ are as defined under the formulae I, II and III, unless expressly stated otherwise.

$R^6$ is preferably alkyl, furthermore preferably alkyl which is substituted by from 1 to 5 fluorine and/or chlorine atoms, furthermore preferably cycloalkyl.

In the above formulae, alkyl is preferably unbranched and has 1, 2, 3, 4, 5, 6, 7, 8, 9 or 10 carbon atoms, preferably 1, 2, 3, 4, 5 or 6 carbon atoms, and is preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, trifluoromethyl, propyl, isopropyl, butyl, n-pentyl, n-hexyl or n-decyl.

Cycloalkyl preferably has 3-7 carbon atoms and is preferably cyclopropyl and cyclobutyl, furthermore preferably cyclopentyl or cyclohexyl, furthermore also cycloheptyl, particularly preferably cyclopentyl.

Alkenyl is preferably allyl, 2- or 3-butenyl, isobutenyl, sec-butenyl, furthermore preferably 4-pentenyl, isopentenyl or 5-hexenyl.

Alkylene is preferably unbranched and is preferably methylene or ethylene, furthermore preferably propylene or butylene.

Alkylenecycloalkyl preferably has 5-10 carbon atoms and is preferably methylenecyclopropyl, methylenecyclobutyl, furthermore preferably methylenecyclopentyl, methylenecyclohexyl or methylenecycloheptyl, furthermore alternatively ethylenecyclopropyl, ethylenecyclobutyl, ethylenecyclopentyl, ethylenecyclohexyl or ethylenecycloheptyl, propylenecyclopentyl, propylenecyclohexyl, butylenecyclopentyl or butylenecyclohexyl.

Hal is preferably F, Cl or Br, but alternatively I.

The radicals $R^1$ and $R^2$ may be identical or different. $R^2$ is preferably in the 3-position of the phenyl ring. The radicals $R^1$ and $R^2$ are, independently of one another, for example, hydroxyl, —S—$CH_3$, —SO—$CH_3$, —$SO_2CH_3$, F, Cl, Br or I or together are methylenedioxy. However, they are preferably each methoxy, ethoxy, propoxy, cyclopentoxy, but also fluoro-, difluoro- or trifluoromethoxy or 1-fluoro-, 2-fluoro-, 1,2-difluoro-, 2,2-difluoro-, 1,2,2-trifluoro- or 2,2,2-trifluoroethoxy.

$R^1$ is particularly preferably methoxy, ethoxy, cyclopentoxy or isopropoxy.

$R^2$ is particularly preferably methoxy or ethoxy.

A is preferably phenyl, 2-, 3- or 4-pyridyl, or 4- or 5-pyrimidyl, particularly preferably phenyl or 2-, 3- or 4-pyridyl, in particular phenyl or 3-pyridyl.

$R^3$ and $R^4$ are preferably in the ortho- and para-position to the —$CH_2S$— group on ring A. The radicals $R^3$ and $R^4$, in the case where A is a heteroaromatic ring, are also always bonded to a carbon atom in the ring. $R^3$ and $R^4$ are in this case particularly preferably each an H atom.

$R^3$ and $R^4$, independently of one another, preferably adopt the meaning of $R^6$ or one of the meanings mentioned for $R^1$ and $R^2$. $R^3$ is particularly preferably methoxy, ethoxy, propoxy, cyclopentoxy, or alternatively fluoro-, difluoro- or trifluoromethoxy or 1-fluoro-, 2-fluoro-, 1,2-difluoro-, 2,2-difluoro-, 1,2,2-trifluoro- or 2,2,2-trifluoroethoxy. $R^4$ is particularly preferably alkoxy or alkyl, in particular methoxy, ethoxy, propoxy, cyclopentoxy or methyl, ethyl, trifluoromethyl, propyl, isopropyl, butyl, n-pentyl, n-hexyl or n-decyl.

$R^5$ is preferably in each case, independently of one another, H or methyl, in particular methyl.

Throughout the invention, all radicals which occur more than once may be identical or different, i.e. are independent of one another.

Accordingly, the invention relates, in particular, to the compounds of the formula I in which at least one of the said radicals has one of the preferred meanings indicated above. Some preferred groups of compounds may be expressed by the following sub-formulae Ia to If, which conform to the formula I and in which the radicals not designated in greater detail have the meaning indicated for the formula I, but in which in Ia $R^1$ and $R^2$ are each, independently of one another, $OR^6$;

in Ib $R^1$ and $R^2$ are each, independently of one another, $OR^6$,
  $R^6$ is alkyl having 1-10 carbon atoms or cycloalkyl having 3-7 carbon atoms;

in Ic $R^1$ and $R^2$ are each, independently of one another, $OR^6$,
  $R^6$ is alkyl having 1-10 carbon atoms or cycloalkyl having 3-7 carbon atoms,
  A is phenyl, 2-, 3- or 4-pyridyl or 4- or 5-pyrimidyl,
  $R^3$ and $R^4$ are each, independently of one another, $R^6$, H, Cl, $CF_3$ or $OR^6$;

in Id $R^1$ and $R^2$ are each, independently of one another, $OR^6$,
  $R^6$ is alkyl having 1-10 carbon atoms or cycloalkyl having 3-7 carbon atoms,
  A is phenyl, 2-, 3- or 4-pyridyl or 4- or 5-pyrimidyl,
  $R^3$ and $R^4$ are each, independently of one another, H, Cl, F, $CF_3$ or $OR^6$,
  $R^5$ is H or methyl;

in Ie $R^1$ and $R^2$ are each, independently of one another, $OR^6$,
  $R^6$ is alkyl having 1-10 carbon atoms or cycloalkyl having 3-7 carbon atoms,
  A is phenyl, 2-, 3- or 4-pyridyl or 4- or 5-pyrimidyl,
  $R^3$ and $R^4$ are each, independently of one another, H, Cl, F, $CF_3$ or $OR^6$,
  $R^5$ is methyl.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ by not isolating them from the reaction mixture, but instead immediately converting them further into the compounds of the formula I.

On the other hand, it is possible to carry out the reaction stepwise.

The compounds of the formula I can preferably be obtained by reacting compounds of the formula II with compounds of the formula III.

Some of the starting materials of the formulae II and III are known (for example U.S. Pat. No. 3,905,801). If they are not known, they can be prepared by methods known per se.

In detail, the reaction of the compounds of the formula II with the compounds of the formula III is carried out in the presence or absence of a preferably inert solvent at temperatures between about −20 and about 150°, preferably between 20 and 100°.

Examples of suitable solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); nitro compounds, such as nitromethane or nitrobenzene; esters, such as ethyl acetate, or mixtures of the said solvents.

In the reaction of compounds of the formula II with compounds of the formula III, it is possible to employ dehydrating agents, as are known for similar reactions of carbonyl compounds with amino compounds, in order to shift the reaction equilibrium to the side of the products. For example, it is possible to use silica gel, molecular sieve, hygroscopic salts, solvents or acids. Water formed during the reaction can likewise be removed from the reaction mixture by conventional methods, such as evaporation or by means of a water separator. The equilibrium can furthermore likewise be shifted by using a solvent in which the starting compounds II and III are dissolved, but the compounds of the formula I are not, so that product formed is removed from the equilibrium.

The pH necessary for the reaction can be set in accordance with pH values selected for similar reactions of carbonyl compounds with amino compounds. A suitable added acid is preferably a carboxylic acid, in particular acetic acid.

A base of the formula I can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, or laurylsulfuric acid. Salts with physiologically unacceptable acids, for example picrates, can be used for the isolation and/or purification of the compounds of the formula I.

On the other hand, if desired, the free bases of the formula I can be liberated from their salts using bases (for example sodium hydroxide, potassium hydroxide, sodium carbonate or potassium carbonate).

The invention relates to compounds of the formula I and physiologically acceptable salts and solvates thereof as medicaments.

The invention also relates to the compounds of the formula I and physiologically acceptable salts and solvates thereof as phosphodiesterase IV inhibitors.

The invention furthermore relates to the use of the compounds of the formula I and/or physiologically acceptable salts and/or solvates thereof for the preparation of pharmaceutical preparations, in particular by non-chemical methods. In this case, they can be converted into a suitable dosage form together with at least one solid, liquid and/or semi-liquid excipient or adjuvant and, if desired, in combination with one or more further active ingredients.

The invention furthermore relates to pharmaceutical preparations comprising at least one compound of the formula I and/or one of its physiologically acceptable salts and/or solvates.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The preparations indicated may be sterilised and/or comprise adjuvants, such as lubricants, preservatives, stabilisers and/or wetting agents, emulsifiers, salts for modifying the osmotic pressure, buffer substances, dyes and flavours and/or one or more further active ingredients, for example one or more vitamins.

The compounds of the formula I and physiologically acceptable salts and solvates thereof can be employed for combating diseases, with an increase in the cAMP (cycloadenosine monophosphate) level being achieved, resulting in inhibition or prevention of inflammation and muscle relaxation. In particular, the PDE IV inhibitors according to the invention can be used in the treatment of allergic diseases, asthma, chronic bronchitis, atopic dermatitis, psoriasis and other skin diseases, inflammatory diseases, autoimmune diseases, such as, for example, rheumatoid arthritis, multiple sclerosis, Crohn's disease, diabetes mellitus or ulcerative colitis, osteoporosis, transplant rejection reactions, cachexia, tumour growth or tumour metastases, sepsis, memory disorders, atherosclerosis and AIDS.

In general, the substances according to the invention are preferably administered in doses corresponding to the compound rolipram of between 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

EXAMPLE I

Effect of the PDE IV Inhibitors of the Formula I on the Proliferation of T-cells Peripheral blood mononuclear cells (PBMC) are isolated from the blood of healthy donors using the Lymphoprep gradient method. 200,000 PBMC/well are cultivated for 5 days at 37° C. and 10% $CO_2$ in microtitre plates with a flat base and 96 wells in RPMI1640 culture medium with 5% of heat-deactivated human serum (AB pool). The T-cells in the PBMC preparation are stimulated selectively against CD3 with a monoclonal antibody. In each case, three batches of the cultures are prepared, including a control group which is not treated. The PDE IV inhibitors of the formula I are dissolved in DMSO to a concentration of $10^{-2}$ M and diluted with culture medium. DMSO is added to the control cultures correspondingly to the inhibitor concentration. 18 hours before the end of the assay, $^3$H-thymidine is added to the cultures. The uptake of radioactivity into the cells is then measured in a beta counter. The data from at least three independent experiments are calculated as percentage inhibition of the control (mean±standard deviation) without inhibitor. The $IC_{50}$ value is determined from these data.

Results:

The PDE IV inhibitors of the formula I cause a significant reduction in T-cell proliferation.

EXAMPLE II

Effect of the PDE IV Inhibitors of the Formula I on Cytokine Production in Human Peripheral Blood Monocytic Cells Peripheral blood mononuclear cells (PBMC) are isolated from the blood of healthy donors using the Lymphoprep gradient method. 200,000 PBMC/well are cultivated at 37° C. and 10% $CO_2$ in microtitre plates with a flat base and 96 wells in RPMI1640 culture medium with 5% of heat-deactivated human serum (AB pool). In each case, three batches of the cultures are prepared, including a control group. $10^{-2}$ M solutions of the PDE IV inhibitors of the formula I in DMSO are prepared and are then diluted with culture medium. DMSO concentrations are added to the control cultures correspondingly to the inhibitor concentration. The relevant cytokine is stimulated.

The culture supernatants from three independent experiments are pooled, and the cytokine activity in the supernatant is measured using a commercially available ELISA test kit. The data are calculated as percentage inhibition/stimulation of the control group without compound, and the corresponding $IC_{50}$ value or $EC_{50}$ value is determined in the case of stimulation.

Result

The PDE IV inhibitors of the formula I cause significantly reduced liberation of IL-2, IFN-γ, TNF-α and IL-12.

EXAMPLE III

Effect of the PDE IV Inhibitors of the Formula I on Experimental Myocardial Infarction in Rats In rats, compound 5 causes a significant, dose-dependent reduction in the infarction size of up to 38% on intraperitoneal administration of 1, 3 or 10 mg/kg 1 hour before reversible closure of the left coronary artery. In agreement with this protection, a reduction, measured by means of ELISA, in the TNF-alpha concentration in the plasma is observed.

EXAMPLE IV Effect of the PDE IV Inhibitors of the Formula I on Experimental Myocardial Infarction in Rabbits In anaesthetised rabbits in which the coronary artery (side arm of the Ramus circumflexus of the left coronary artery) is closed for 30 minutes and subsequently re-perfused for 120 minutes, PDE IV inhibition has a cardioprotective action. Compared with placebo, PDE IV inhibitors of the formula I administered before the coronary closure reduced the infarction size. The endangered regions were comparable in the verum and placebo groups. The cardioprotective action can be ascribed to unfavourable haemodynamic effects since the heart rate and mean aortal pressure remain constant during performance of the experiment.

Above and below, all temperatures are given in ° C. In the following examples, "conventional work-up" means that water is added if necessary, the pH is adjusted, if necessary, to values of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. The terms ortho (o), meta (m) and para (p) relate to the —$CH_2S$— or —CHN— group located on the rings.

EXAMPLE 1

0.272 g of 4-amino-3-mercapto-6-methyl-4H-1,2,4-triazin-5-one (which can be prepared by the method of A. Dornow, H. Menzel, P. Marx, Chem. Ber. 97, 2173 (1964)) was suspended in 0.86 ml of a 2N solution of sodium hydroxide in water. A solution of 0.218 g of benzyl chloride in ethanol was subsequently added dropwise, and the mixture was heated at 80° C. for 30 minutes. The resultant precipitate was filtered off with suction, giving 4-amino-3-benzylsulfanyl-6-methyl-4H-1,2,4-triazin-5-one.

The following compounds of the formula IIIa are obtained analogously using the corresponding precursors:

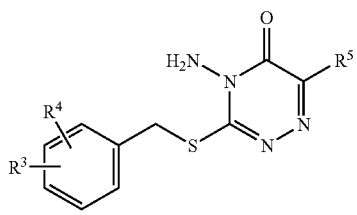

IIIa

|     | $R^3$ | $R^4$ | $R^5$ |
|-----|-------|-------|-------|
| (2) | o-F   | H     | $CH_3$ |
| (3) | m-F   | H     | $CH_3$ |
| (4) | p-F   | H     | $CH_3$ |

-continued

IIIa

|     | $R^3$ | $R^4$ | $R^5$ |
|-----|-------|-------|-------|
| (5) | o-Cl | H | $CH_3$ |
| (6) | m-Cl | H | $CH_3$ |
| (7) | p-Cl | H | $CH_3$ |
| (8) | o-Cl | o-Cl | $CH_3$ |
| (9) | m-Cl | o-Cl | $CH_3$ |
| (10) | p-Cl | o-Cl | $CH_3$ |
| (11) | m-Cl | m-Cl | $CH_3$ |
| (12) | p-Cl | m-Cl | $CH_3$ |
| (13) | o-Cl | o-F | $CH_3$ |
| (14) | m-Cl | o-F | $CH_3$ |
| (15) | p-Cl | o-F | $CH_3$ |
| (16) | o-Cl | m-F | $CH_3$ |
| (17) | m-Cl | m-F | $CH_3$ |
| (18) | p-Cl | m-F | $CH_3$ |
| (19) | o-Cl | p-F | $CH_3$ |
| (20) | m-Cl | p-F | $CH_3$ |
| (21) | o-F | o-F | $CH_3$ |
| (22) | m-F | o-F | $CH_3$ |
| (23) | p-F | o-F | $CH_3$ |
| (24) | m-F | m-F | $CH_3$ |
| (25) | p-F | m-F | $CH_3$ |
| (26) | o-$OCH_3$ | H | $CH_3$ |
| (27) | m-$OCH_3$ | H | $CH_3$ |
| (28) | p-$OCH_3$ | H | $CH_3$ |
| (29) | o-$OCH_3$ | o-Cl | $CH_3$ |
| (30) | m-$OCH_3$ | o-Cl | $CH_3$ |
| (31) | p-$OCH_3$ | o-Cl | $CH_3$ |
| (32) | m-$OCH_3$ | m-Cl | $CH_3$ |
| (33) | p-$OCH_3$ | m-Cl | $CH_3$ |
| (34) | o-$OCH_3$ | o-F | $CH_3$ |
| (35) | m-$OCH_3$ | o-F | $CH_3$ |
| (36) | p-$OCH_3$ | o-F | $CH_3$ |
| (37) | o-$OCH_3$ | m-F | $CH_3$ |
| (38) | m-$OCH_3$ | m-F | $CH_3$ |
| (39) | p-$OCH_3$ | m-F | $CH_3$ |
| (40) | o-$OCH_3$ | p-F | $CH_3$ |
| (41) | m-$OCH_3$ | p-F | $CH_3$ |
| (42) | o-$OCH_3$ | o-$OCH_3$ | $CH_3$ |
| (43) | m-$OCH_3$ | o-$OCH_3$ | $CH_3$ |
| (44) | p-$OCH_3$ | o-$OCH_3$ | $CH_3$ |
| (45) | m-$OCH_3$ | m-$OCH_3$ | $CH_3$ |
| (46) | p-$OCH_3$ | m-$OCH_3$ | $CH_3$ |
| (47) | o-OH | H | $CH_3$ |
| (48) | m-OH | H | $CH_3$ |
| (49) | p-OH | H | $CH_3$ |
| (50) | o-OH | o-Cl | $CH_3$ |
| (51) | m-OH | o-Cl | $CH_3$ |
| (52) | p-OH | o-Cl | $CH_3$ |
| (53) | m-OH | m-Cl | $CH_3$ |
| (54) | p-OH | m-Cl | $CH_3$ |
| (55) | o-OH | o-F | $CH_3$ |
| (56) | m-OH | o-F | $CH_3$ |
| (57) | p-OH | o-F | $CH_3$ |
| (58) | o-OH | m-F | $CH_3$ |
| (59) | m-OH | m-F | $CH_3$ |
| (60) | p-OH | m-F | $CH_3$ |
| (61) | o-OH | p-F | $CH_3$ |
| (62) | m-OH | p-F | $CH_3$ |
| (63) | o-OH | o-OH | $CH_3$ |
| (64) | m-OH | o-OH | $CH_3$ |
| (65) | p-OH | o-OH | $CH_3$ |
| (66) | m-OH | m-OH | $CH_3$ |
| (67) | p-OH | m-OH | $CH_3$ |
| (68) | o-$CH_3$ | H | $CH_3$ |
| (69) | m-$CH_3$ | H | $CH_3$ |

-continued

IIIa

Structure: H₂N-N / C=O / R⁵ substituent on 1,2,4-triazinone ring; S-CH₂-phenyl with R³, R⁴ on phenyl ring.

| | R³ | R⁴ | R⁵ |
|---|---|---|---|
| (70) | p-CH₃ | H | CH₃ |
| (71) | o-CH₃ | o-Cl | CH₃ |
| (72) | m-CH₃ | o-Cl | CH₃ |
| (73) | p-CH₃ | o-Cl | CH₃ |
| (74) | m-CH₃ | m-Cl | CH₃ |
| (75) | p-CH₃ | m-Cl | CH₃ |
| (76) | o-CH₃ | o-F | CH₃ |
| (77) | m-CH₃ | o-F | CH₃ |
| (78) | p-CH₃ | o-F | CH₃ |
| (79) | o-CH₃ | m-F | CH₃ |
| (80) | m-CH₃ | m-F | CH₃ |
| (81) | p-CH₃ | m-F | CH₃ |
| (82) | o-CH₃ | p-F | CH₃ |
| (83) | m-CH₃ | p-F | CH₃ |
| (84) | o-CH₃ | o-CH₃ | CH₃ |
| (85) | m-CH₃ | o-CH₃ | CH₃ |
| (86) | p-CH₃ | o-CH₃ | CH₃ |
| (87) | m-CH₃ | m-CH₃ | CH₃ |
| (88) | p-CH₃ | m-CH₃ | CH₃ |
| (89) | o-F | H | C₂H₅ |
| (90) | m-F | H | C₂H₅ |
| (91) | p-F | H | C₂H₅ |
| (92) | o-Cl | H | C₂H₅ |
| (93) | m-Cl | H | C₂H₅ |
| (94) | p-Cl | H | C₂H₅ |
| (95) | o-Cl | o-Cl | C₂H₅ |
| (96) | m-Cl | o-Cl | C₂H₅ |
| (97) | p-Cl | o-Cl | C₂H₅ |
| (98) | m-Cl | m-Cl | C₂H₅ |
| (99) | p-Cl | m-Cl | C₂H₅ |
| (100) | o-Cl | o-F | C₂H₅ |
| (101) | m-Cl | o-F | C₂H₅ |
| (102) | p-Cl | o-F | C₂H₅ |
| (103) | o-Cl | m-F | C₂H₅ |
| (104) | m-Cl | m-F | C₂H₅ |
| (105) | p-Cl | m-F | C₂H₅ |
| (106) | o-Cl | p-F | C₂H₅ |
| (107) | m-Cl | p-F | C₂H₅ |
| (108) | o-F | o-F | C₂H₅ |
| (109) | m-F | o-F | C₂H₅ |
| (110) | p-F | o-F | C₂H₅ |
| (111) | m-F | m-F | C₂H₅ |
| (112) | p-F | m-F | C₂H₅ |
| (113) | o-OCH₃ | H | C₂H₅ |
| (114) | m-OCH₃ | H | C₂H₅ |
| (115) | p-OCH₃ | H | C₂H₅ |
| (116) | o-OCH₃ | o-Cl | C₂H₅ |
| (117) | m-OCH₃ | o-Cl | C₂H₅ |
| (118) | p-OCH₃ | o-Cl | C₂H₅ |
| (119) | m-OCH₃ | m-Cl | C₂H₅ |
| (120) | p-OCH₃ | m-Cl | C₂H₅ |
| (121) | o-OCH₃ | o-F | C₂H₅ |
| (122) | m-OCH₃ | o-F | C₂H₅ |
| (123) | p-OCH₃ | o-F | C₂H₅ |
| (124) | o-OCH₃ | m-F | C₂H₅ |
| (125) | m-OCH₃ | m-F | C₂H₅ |
| (126) | p-OCH₃ | m-F | C₂H₅ |
| (127) | o-OCH₃ | p-F | C₂H₅ |
| (128) | m-OCH₃ | p-F | C₂H₅ |
| (129) | o-OCH₃ | o-OCH₃ | C₂H₅ |
| (130) | m-OCH₃ | o-OCH₃ | C₂H₅ |
| (131) | p-OCH₃ | o-OCH₃ | C₂H₅ |
| (132) | m-OCH₃ | m-OCH₃ | C₂H₅ |
| (133) | p-OCH₃ | m-OCH₃ | C₂H₅ |
| (134) | o-OH | H | C₂H₅ |
| (135) | m-OH | H | C₂H₅ |
| (136) | p-OH | H | C₂H₅ |
| (137) | o-OH | o-Cl | C₂H₅ |
| (138) | m-OH | o-Cl | C₂H₅ |
| (139) | p-OH | o-Cl | C₂H₅ |
| (140) | m-OH | m-Cl | C₂H₅ |
| (141) | p-OH | m-Cl | C₂H₅ |
| (142) | o-OH | o-F | C₂H₅ |
| (143) | m-OH | o-F | C₂H₅ |
| (144) | p-OH | o-F | C₂H₅ |
| (145) | o-OH | m-F | C₂H₅ |
| (146) | m-OH | m-F | C₂H₅ |
| (147) | p-OH | m-F | C₂H₅ |
| (148) | o-OH | p-F | C₂H₅ |
| (149) | m-OH | p-F | C₂H₅ |
| (150) | o-OH | o-OH | C₂H₅ |
| (151) | m-OH | o-OH | C₂H₅ |
| (152) | p-OH | o-OH | C₂H₅ |
| (153) | m-OH | m-OH | C₂H₅ |
| (154) | p-OH | m-OH | C₂H₅ |
| (155) | o-CH₃ | H | C₂H₅ |
| (156) | m-CH₃ | H | C₂H₅ |
| (157) | p-CH₃ | H | C₂H₅ |
| (158) | o-CH₃ | o-Cl | C₂H₅ |
| (159) | m-CH₃ | o-Cl | C₂H₅ |
| (160) | p-CH₃ | o-Cl | C₂H₅ |
| (161) | m-CH₃ | m-Cl | C₂H₅ |
| (162) | p-CH₃ | m-Cl | C₂H₅ |
| (163) | o-CH₃ | o-F | C₂H₅ |
| (164) | m-CH₃ | o-F | C₂H₅ |
| (165) | p-CH₃ | o-F | C₂H₅ |
| (166) | o-CH₃ | m-F | C₂H₅ |
| (167) | m-CH₃ | m-F | C₂H₅ |
| (168) | p-CH₃ | m-F | C₂H₅ |
| (169) | o-CH₃ | p-F | C₂H₅ |
| (170) | m-CH₃ | p-F | C₂H₅ |
| (171) | o-CH₃ | o-CH₃ | C₂H₅ |
| (172) | m-CH₃ | o-CH₃ | C₂H₅ |
| (173) | p-CH₃ | o-CH₃ | C₂H₅ |
| (174) | m-CH₃ | m-CH₃ | C₂H₅ |
| (175) | p-CH₃ | m-CH₃ | C₂H₅ |

The following compounds of the formula IIIb are obtained analogously using the corresponding precursors:

IIIb

[Structure: 4-amino-triazinone with S-CH2-pyridine (R3,R4 on pyridine), R5 on triazinone]

| | R³ | R⁴ | R⁵ |
|---|---|---|---|
| (176) | o-F | H | CH₃ |
| (177) | m-F | H | CH₃ |
| (178) | p-F | H | CH₃ |
| (179) | o-Cl | H | CH₃ |
| (180) | m-Cl | H | CH₃ |
| (181) | p-Cl | H | CH₃ |
| (182) | H | H | CH₃ |
| (183) | o-OCH₃ | H | CH₃ |
| (184) | m-OCH₃ | H | CH₃ |
| (185) | p-OCH₃ | H | CH₃ |

The following compounds of the formula IIIc are obtained analogously using the corresponding precursors:

IIIc

[Structure: 4-amino-triazinone with S-CH2-pyridine (different regiochemistry), R5 on triazinone]

| | R³ | R⁴ | R⁵ |
|---|---|---|---|
| (186) | o-F | H | CH₃ |
| (187) | m-F | H | CH₃ |
| (188) | o-Cl | H | CH₃ |
| (189) | m-Cl | H | CH₃ |
| (190) | H | H | CH₃ |
| (191) | o-OCH₃ | H | CH₃ |
| (192) | m-OCH₃ | H | CH₃ |

EXAMPLE 193

0.054 g of 3-ethoxy-4-methoxybenzaldehyde and 0.017 ml of acetic acid were added to a solution of 0.080 g of 4-amino-3-(2-fluorobenzylsulfanyl)-6-methyl-4H-1,2,4-triazin-5-one in 4 ml of ethanol, and the mixture was stirred at 65° C. The resultant precipitate was filtered off with suction, giving 4-[(3-ethoxy-4-methoxybenzylidene)amino]-3-(2-fluorobenzylsulfanyl)-6-methyl-4H-1,2,4-triazin-5-one.

The following compounds of the formula Ia are obtained analogously using the corresponding starting compounds:

Ia

[Structure: benzylidene-amino-triazinone with S-CH2-aryl]

| | R¹ | R² | R³ | R⁴ | R⁵ | |
|---|---|---|---|---|---|---|
| (194) | OCH₃ | m-OC₂H₅ | H | H | CH₃ | |
| (195) | OCH₃ | m-OC₂H₅ | o-Cl | H | CH₃ | (m.p. 157° C.) |
| (196) | OCH₃ | m-OC₂H₅ | m-Cl | H | CH₃ | |
| (197) | OCH₃ | m-OC₂H₅ | p-Cl | H | CH₃ | |
| (198) | OCH₃ | m-OC₂H₅ | o-F | H | CH₃ | (m.p. 155° C.) |
| (199) | OCH₃ | m-OC₂H₅ | m-F | H | CH₃ | |
| (200) | OCH₃ | m-OC₂H₅ | p-F | H | CH₃ | |
| (201) | OCH₃ | m-OC₂H₅ | o-Cl | o-Cl | CH₃ | |
| (202) | OCH₃ | m-OC₂H₅ | m-Cl | o-Cl | CH₃ | |
| (203) | OCH₃ | m-OC₂H₅ | p-Cl | o-Cl | CH₃ | |
| (204) | OCH₃ | m-OC₂H₅ | m-Cl | m-Cl | CH₃ | |
| (205) | OCH₃ | m-OC₂H₅ | p-Cl | m-Cl | CH₃ | |
| (206) | OCH₃ | m-OC₂H₅ | o-Cl | o-F | CH₃ | (m.p. 234° C.) |
| (207) | OCH₃ | m-OC₂H₅ | m-Cl | o-F | CH₃ | |
| (208) | OCH₃ | m-OC₂H₅ | p-Cl | o-F | CH₃ | |
| (209) | OCH₃ | m-OC₂H₅ | o-Cl | m-F | CH₃ | |
| (210) | OCH₃ | m-OC₂H₅ | m-Cl | m-F | CH₃ | |
| (211) | OCH₃ | m-OC₂H₅ | p-Cl | m-F | CH₃ | |
| (212) | OCH₃ | m-OC₂H₅ | o-Cl | p-F | CH₃ | |

-continued

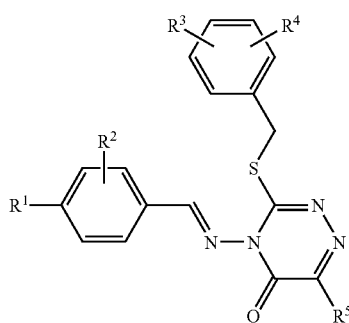
Ia

| | R¹ | R² | R³ | R⁴ | R⁵ |
|---|---|---|---|---|---|
| (213) | OCH₃ | m-OC₂H₅ | m-Cl | p-F | CH₃ |
| (214) | OCH₃ | m-OC₂H₅ | o-F | o-F | CH₃ |
| (215) | OCH₃ | m-OC₂H₅ | m-F | o-F | CH₃ |
| (216) | OCH₃ | m-OC₂H₅ | p-F | o-F | CH₃ |
| (217) | OCH₃ | m-OC₂H₅ | m-F | m-F | CH₃ |
| (218) | OCH₃ | m-OC₂H₅ | p-F | m-F | CH₃ |
| (219) | OCH₃ | m-OC₂H₅ | o-OCH₃ | H | CH₃ |
| (220) | OCH₃ | m-OC₂H₅ | m-OCH₃ | H | CH₃ |
| (221) | OCH₃ | m-OC₂H₅ | p-OCH₃ | H | CH₃ |
| (222) | OCH₃ | m-OC₂H₅ | o-OCH₃ | o-Cl | CH₃ |
| (223) | OCH₃ | m-OC₂H₅ | m-OCH₃ | o-Cl | CH₃ |
| (224) | OCH₃ | m-OC₂H₅ | p-OCH₃ | o-Cl | CH₃ |
| (225) | OCH₃ | m-OC₂H₅ | m-OCH₃ | m-Cl | CH₃ |
| (226) | OCH₃ | m-OC₂H₅ | p-OCH₃ | m-Cl | CH₃ |
| (227) | OCH₃ | m-OC₂H₅ | o-OCH₃ | o-F | CH₃ |
| (228) | OCH₃ | m-OC₂H₅ | m-OCH₃ | o-F | CH₃ |
| (229) | OOH₃ | m-OC₂H₅ | p-OCH₃ | o-F | CH₃ |
| (230) | OCH₃ | m-OC₂H₅ | o-OCH₃ | m-F | CH₃ |
| (231) | OCH₃ | m-OC₂H₅ | m-OCH₃ | m-F | CH₃ |
| (232) | OCH₃ | m-OC₂H₅ | p-OCH₃ | m-F | CH₃ |
| (233) | OCH₃ | m-OC₂H₅ | o-OCH₃ | p-F | CH₃ |
| (234) | OOH₃ | m-OC₂H₅ | m-OCH₃ | p-F | CH₃ |
| (235) | OCH₃ | m-OC₂H₅ | o-OCH₃ | o-OCH₃ | CH₃ |
| (236) | OCH₃ | m-OC₂H₅ | m-OCH₃ | o-OCH₃ | CH₃ |
| (237) | OCH₃ | m-OC₂H₅ | p-OCH₃ | o-OCH₃ | CH₃ |
| (238) | OCH₃ | m-OC₂H₅ | m-OCH₃ | m-OCH₃ | CH₃ |
| (239) | OCH₃ | m-OC₂H₅ | p-OCH₃ | m-OCH₃ | CH₃ |
| (240) | OCH₃ | m-OC₂H₅ | o-OH | H | CH₃ |
| (241) | OOH₃ | m-OC₂H₅ | m-OH | H | CH₃ |
| (242) | OCH₃ | m-OC₂H₅ | p-OH | H | CH₃ |
| (243) | OCH₃ | m-OC₂H₅ | o-OH | o-Cl | CH₃ |
| (244) | OCH₃ | m-OC₂H₅ | m-OH | o-Cl | CH₃ |
| (245) | OCH₃ | m-OC₂H₅ | p-OH | o-Cl | CH₃ |
| (246) | OCH₃ | m-OC₂H₅ | m-OH | m-Cl | CH₃ |
| (247) | OCH₃ | m-OC₂H₅ | p-OH | m-Cl | CH₃ |
| (248) | OCH₃ | m-OC₂H₅ | o-OH | o-F | CH₃ |
| (249) | OCH₃ | m-OC₂H₅ | m-OH | o-F | CH₃ |
| (250) | OCH₃ | m-OC₂H₅ | p-OH | o-F | CH₃ |
| (251) | OCH₃ | m-OC₂H₅ | o-OH | m-F | CH₃ |
| (252) | OCH₃ | m-OC₂H₅ | m-OH | m-F | CH₃ |
| (253) | OCH₃ | m-OC₂H₅ | p-OH | m-F | CH₃ |
| (254) | OCH₃ | m-OC₂H₅ | o-OH | p-F | CH₃ |
| (255) | OCH₃ | m-OC₂H₅ | m-OH | p-F | CH₃ |
| (256) | OCH₃ | m-OC₂H₅ | o-OH | o-OH | CH₃ |
| (257) | OCH₃ | m-OC₂H₅ | m-OH | o-OH | CH₃ |
| (258) | OCH₃ | m-OC₂H₅ | p-OH | o-OH | CH₃ |
| (259) | OCH₃ | m-OC₂H₅ | m-OH | m-OH | CH₃ |
| (260) | OCH₃ | m-OC₂H₅ | p-OH | m-OH | CH₃ |
| (261) | OCH₃ | m-OC₂H₅ | o-CH₃ | H | CH₃ |
| (262) | OCH₃ | m-OC₂H₅ | m-CH₃ | H | CH₃ |
| (263) | OCH₃ | m-OC₂H₅ | p-CH₃ | H | CH₃ |
| (264) | OCH₃ | m-OC₂H₅ | o-CH₃ | o-Cl | CH₃ |
| (265) | OCH₃ | m-OC₂H₅ | m-CH₃ | o-Cl | CH₃ |
| (266) | OCH₃ | m-OC₂H₅ | p-CH₃ | o-Cl | CH₃ |
| (267) | OCH₃ | m-OC₂H₅ | m-CH₃ | m-Cl | CH₃ |
| (268) | OCH₃ | m-OC₂H₅ | p-CH₃ | m-Cl | CH₃ |
| (269) | OCH₃ | m-OC₂H₅ | o-CH₃ | o-F | CH₃ |
| (270) | OCH₃ | m-OC₂H₅ | m-CH₃ | o-F | CH₃ |
| (271) | OCH₃ | m-OC₂H₅ | p-CH₃ | o-F | CH₃ |
| (272) | OCH₃ | m-OC₂H₅ | o-CH₃ | m-F | CH₃ |

-continued

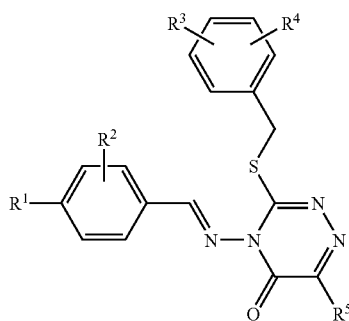
Ia

| | R¹ | R² | R³ | R⁴ | R⁵ |
|---|---|---|---|---|---|
| (273) | OCH₃ | m-OC₂H₅ | m-CH₃ | m-F | CH₃ |
| (274) | OCH₃ | m-OC₂H₅ | p-CH₃ | m-F | CH₃ |
| (275) | OCH₃ | m-OC₂H₅ | o-CH₃ | p-F | CH₃ |
| (276) | OCH₃ | m-OC₂H₅ | m-CH₃ | p-F | CH₃ |
| (277) | OCH₃ | m-OC₂H₅ | o-CH₃ | o-CH₃ | CH₃ |
| (278) | OCH₃ | m-OC₂H₅ | m-CH₃ | o-CH₃ | CH₃ |
| (279) | OCH₃ | m-OC₂H₅ | p-CH₃ | o-CH₃ | CH₃ |
| (280) | OCH₃ | m-OC₂H₅ | m-CH₃ | m-CH₃ | CH₃ |
| (281) | OCH₃ | m-OC₂H₅ | p-CH₃ | m-CH₃ | CH₃ |
| (282) | OCH₃ | o-OC₂H₅ | H | H | CH₃ |
| (283) | OCH₃ | o-OC₂H₅ | o-Cl | H | CH₃ |
| (284) | OCH₃ | o-OC₂H₅ | m-Cl | H | CH₃ |
| (285) | OCH₃ | o-OC₂H₅ | p-Cl | H | CH₃ |
| (286) | OCH₃ | o-OC₂H₅ | o-Cl | o-Cl | CH₃ |
| (287) | OCH₃ | o-OC₂H₅ | m-Cl | o-Cl | CH₃ |
| (288) | OCH₃ | o-OC₂H₅ | p-Cl | o-Cl | CH₃ |
| (289) | OCH₃ | o-OC₂H₅ | m-Cl | m-Cl | CH₃ |
| (290) | OCH₃ | o-OC₂H₅ | p-Cl | m-Cl | CH₃ |
| (291) | OCH₃ | o-OC₂H₅ | o-Cl | o-F | CH₃ |
| (292) | OCH₃ | o-OC₂H₅ | m-Cl | o-F | CH₃ |
| (293) | OCH₃ | o-OC₂H₅ | p-Cl | o-F | CH₃ |
| (294) | OCH₃ | o-OC₂H₅ | o-Cl | m-F | CH₃ |
| (295) | OCH₃ | o-OC₂H₅ | m-Cl | m-F | CH₃ |
| (296) | OCH₃ | o-OC₂H₅ | p-Cl | m-F | CH₃ |
| (297) | OCH₃ | o-OC₂H₅ | o-Cl | p-F | CH₃ |
| (298) | OCH₃ | o-OC₂H₅ | m-Cl | p-F | CH₃ |
| (299) | OCH₃ | o-OC₂H₅ | o-F | o-F | CH₃ |
| (300) | OCH₃ | o-OC₂H₅ | m-F | o-F | CH₃ |
| (301) | OCH₃ | o-OC₂H₅ | p-F | o-F | CH₃ |
| (302) | OCH₃ | o-OC₂H₅ | m-F | m-F | CH₃ |
| (303) | OCH₃ | o-OC₂H₅ | p-F | m-F | CH₃ |
| (304) | OCH₃ | o-OC₂H₅ | o-OCH₃ | H | CH₃ |
| (305) | OCH₃ | o-OC₂H₅ | m-OCH₃ | H | CH₃ |
| (306) | OCH₃ | o-OC₂H₅ | p-OCH₃ | H | CH₃ |
| (307) | OCH₃ | o-OC₂H₅ | o-OCH₃ | o-Cl | CH₃ |
| (308) | OCH₃ | o-OC₂H₅ | m-OCH₃ | o-Cl | CH₃ |
| (309) | OCH₃ | o-OC₂H₅ | p-OCH₃ | o-Cl | CH₃ |
| (310) | OCH₃ | o-OC₂H₅ | m-OCH₃ | m-Cl | CH₃ |
| (311) | OCH₃ | o-OC₂H₅ | p-OCH₃ | m-Cl | CH₃ |
| (312) | OCH₃ | o-OC₂H₅ | o-OCH₃ | o-F | CH₃ |
| (313) | OCH₃ | o-OC₂H₅ | m-OCH₃ | o-F | CH₃ |
| (314) | OCH₃ | o-OC₂H₅ | p-OCH₃ | o-F | CH₃ |
| (315) | OCH₃ | o-OC₂H₅ | o-OCH₃ | m-F | CH₃ |
| (316) | OCH₃ | o-OC₂H₅ | m-OCH₃ | m-F | CH₃ |
| (317) | OCH₃ | o-OC₂H₅ | p-OCH₃ | m-F | CH₃ |
| (318) | OCH₃ | o-OC₂H₅ | o-OCH₃ | p-F | CH₃ |
| (319) | OCH₃ | o-OC₂H₅ | m-OCH₃ | p-F | CH₃ |
| (320) | OCH₃ | o-OC₂H₅ | o-OCH₃ | o-OCH₃ | CH₃ |
| (321) | OOH₃ | o-OC₂H₅ | m-OCH₃ | o-OCH₃ | CH₃ |
| (322) | OCH₃ | o-OC₂H₅ | p-OCH₃ | o-OCH₃ | CH₃ |
| (323) | OCH₃ | o-OC₂H₅ | m-OCH₃ | m-OCH₃ | CH₃ |
| (324) | OCH₃ | o-OC₂H₅ | p-OCH₃ | m-OCH₃ | CH₃ |
| (325) | OCH₃ | o-OC₂H₅ | o-OH | H | CH₃ |
| (326) | OCH₃ | o-OC₂H₅ | m-OH | H | CH₃ |
| (327) | OCH₃ | a-OC₂H₅ | p-OH | H | CH₃ |
| (328) | OCH₃ | o-OC₂H₅ | o-OH | o-Cl | CH₃ |
| (329) | OCH₃ | o-OC₂H₅ | m-OH | o-Cl | CH₃ |
| (330) | OCH₃ | o-OC₂H₅ | p-OH | o-Cl | CH₃ |
| (331) | OCH₃ | o-OC₂H₅ | m-OH | m-Cl | CH₃ |
| (332) | OCH₃ | o-OC₂H₅ | p-OH | m-Cl | CH₃ |

-continued

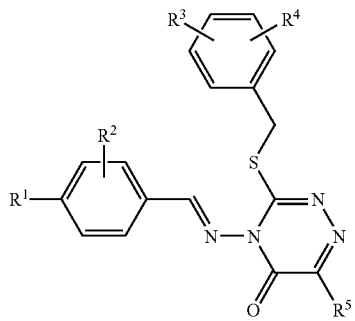
Ia

| | R¹ | R² | R³ | R⁴ | R⁵ |
|---|---|---|---|---|---|
| (333) | OCH₃ | o-OC₂H₅ | o-OH | o-F | CH₃ |
| (334) | OCH₃ | o-OC₂H₅ | m-OH | o-F | CH₃ |
| (335) | OCH₃ | o-OC₂H₅ | p-OH | o-F | CH₃ |
| (336) | OCH₃ | o-OC₂H₅ | o-OH | m-F | CH₃ |
| (337) | OCH₃ | o-OC₂H₅ | m-OH | m-F | CH₃ |
| (338) | OCH₃ | o-OC₂H₅ | p-OH | m-F | CH₃ |
| (339) | OCH₃ | o-OC₂H₅ | o-OH | p-F | CH₃ |
| (340) | OCH₃ | o-OC₂H₅ | m-OH | p-F | CH₃ |
| (341) | OCH₃ | o-OC₂H₅ | o-OH | o-OH | CH₃ |
| (342) | OCH₃ | o-OC₂H₅ | m-OH | o-OH | CH₃ |
| (343) | OCH₃ | o-OC₂H₅ | p-OH | o-OH | CH₃ |
| (344) | OCH₃ | o-OC₂H₅ | m-OH | m-OH | CH₃ |
| (345) | OCH₃ | o-OC₂H₅ | p-OH | m-OH | CH₃ |
| (346) | OCH₃ | o-OC₂H₅ | o-CH₃ | H | CH₃ |
| (347) | OCH₃ | o-OC₂H₅ | m-CH₃ | H | CH₃ |
| (348) | OCH₃ | o-OC₂H₅ | p-CH₃ | H | CH₃ |
| (349) | OCH₃ | o-OC₂H₅ | o-CH₃ | o-Cl | CH₃ |
| (350) | OCH₃ | o-OC₂H₅ | m-CH₃ | o-Cl | CH₃ |
| (351) | OCH₃ | o-OC₂H₅ | p-CH₃ | o-Cl | CH₃ |
| (352) | OCH₃ | o-OC₂H₅ | m-CH₃ | m-Cl | CH₃ |
| (353) | OCH₃ | o-OC₂H₅ | p-CH₃ | m-Cl | CH₃ |
| (354) | OCH₃ | o-OC₂H₅ | o-CH₃ | o-F | CH₃ |
| (355) | OCH₃ | o-OC₂H₅ | m-CH₃ | o-F | CH₃ |
| (356) | OCH₃ | o-OC₂H₅ | p-CH₃ | o-F | CH₃ |
| (357) | OCH₃ | o-OC₂H₅ | o-CH₃ | m-F | CH₃ |
| (358) | OCH₃ | o-OC₂H₅ | m-CH₃ | m-F | CH₃ |
| (359) | OCH₃ | o-OC₂H₅ | p-CH₃ | m-F | CH₃ |
| (360) | OCH₃ | o-OC₂H₅ | o-CH₃ | p-F | CH₃ |
| (361) | OCH₃ | o-OC₂H₅ | m-CH₃ | p-F | CH₃ |
| (362) | OCH₃ | o-OC₂H₅ | o-CH₃ | o-CH₃ | CH₃ |
| (363) | OCH₃ | o-OC₂H₅ | m-CH₃ | o-CH₃ | CH₃ |
| (364) | OCH3 | o-OC₂H₅ | p-CH₃ | o-CH₃ | CH₃ |
| (365) | OCH3 | o-OC₂H₅ | m-CH₃ | m-CH₃ | CH₃ |
| (366) | OCH3 | o-OC₂H₅ | p-CH₃ | m-CH₃ | CH₃ |
| (367) | OCH₃ | m-OCH₃ | H | H | CH₃ |
| (368) | OCH₃ | m-OCH₃ | o-Cl | H | CH₃ |
| (369) | OCH₃ | m-OCH₃ | m-Cl | H | CH₃ |
| (370) | OCH₃ | m-OCH₃ | p-Cl | H | CH₃ |
| (371) | OCH₃ | m-OCH₃ | o-Cl | o-Cl | CH₃ |
| (372) | OCH₃ | m-OCH₃ | m-Cl | o-Cl | CH₃ |
| (373) | OCH₃ | m-OCH₃ | p-Cl | o-Cl | CH₃ |
| (374) | OCH₃ | m-OCH₃ | m-Cl | m-Cl | CH₃ |
| (375) | OCH₃ | m-OCH₃ | p-Cl | m-Cl | CH₃ |
| (376) | OCH₃ | m-OCH₃ | o-Cl | o-F | CH₃ |
| (377) | OCH₃ | m-OCH₃ | m-Cl | o-F | CH₃ |
| (378) | OCH₃ | m-OCH₃ | p-Cl | o-F | CH₃ |
| (379) | OCH₃ | m-OCH₃ | o-Cl | m-F | CH₃ |
| (380) | OCH₃ | m-OCH₃ | m-Cl | m-F | CH₃ |
| (381) | OCH₃ | m-OCH₃ | p-Cl | m-F | CH₃ |
| (382) | OCH₃ | m-OCH₃ | o-Cl | p-F | CH₃ |
| (383) | OCH₃ | m-OCH₃ | m-Cl | p-F | CH₃ |
| (384) | OCH₃ | m-OCH₃ | o-F | o-F | CH₃ |
| (385) | OCH₃ | m-OCH₃ | m-F | o-F | CH₃ |
| (386) | OCH₃ | m-OCH₃ | p-F | o-F | CH₃ |
| (387) | OCH₃ | m-OCH₃ | m-F | m-F | CH₃ |
| (388) | OCH₃ | m-OCH₃ | p-F | m-F | CH₃ |
| (389) | OCH₃ | m-OCH₃ | o-OCH₃ | H | CH₃ |
| (390) | OCH₃ | m-OCH₃ | m-OCH₃ | H | CH₃ |
| (391) | OCH₃ | m-OCH₃ | p-OCH₃ | H | CH₃ |
| (392) | OCH₃ | m-OCH₃ | o-OCH₃ | o-Cl | CH₃ |

-continued

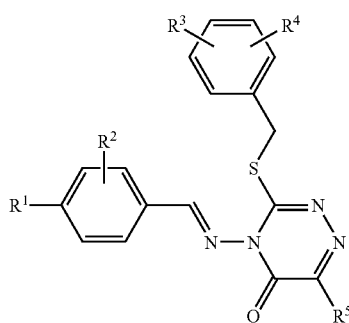

Ia

| | R¹ | R² | R³ | R⁴ | R⁵ |
|---|---|---|---|---|---|
| (393) | OCH₃ | m-OCH₃ | m-OCH₃ | o-Cl | CH₃ |
| (394) | OCH₃ | m-OCH₃ | p-OCH₃ | o-Cl | CH₃ |
| (395) | OCH₃ | m-OCH₃ | m-OCH₃ | m-Cl | CH₃ |
| (396) | OCH₃ | m-OCH₃ | p-OCH₃ | m-Cl | CH₃ |
| (397) | OCH₃ | m-OCH₃ | o-OCH₃ | o-F | CH₃ |
| (398) | OCH₃ | m-OCH₃ | m-OCH₃ | o-F | CH₃ |
| (399) | OCH₃ | m-OCH₃ | p-OCH₃ | o-F | CH₃ |
| (400) | OCH₃ | m-OCH₃ | o-OCH₃ | m-F | CH₃ |
| (401) | OCH₃ | m-OCH₃ | m-OCH₃ | m-F | CH₃ |
| (402) | OCH₃ | m-OCH₃ | p-OCH₃ | m-F | CH₃ |
| (403) | OCH₃ | m-OCH₃ | o-OCH₃ | p-F | CH₃ |
| (404) | OCH₃ | m-OCH₃ | m-OCH₃ | p-F | CH₃ |
| (405) | OCH₃ | m-OCH₃ | o-OCH₃ | o-OCH₃ | CH₃ |
| (406) | OCH₃ | m-OCH₃ | m-OCH₃ | o-OCH₃ | CH₃ |
| (407) | OCH₃ | m-OCH₃ | p-OCH₃ | o-OCH₃ | CH₃ |
| (408) | OCH₃ | m-OCH₃ | m-OCH₃ | m-OCH₃ | CH₃ |
| (409) | OCH₃ | m-OCH₃ | p-OCH₃ | m-OCH₃ | CH₃ |
| (410) | OCH₃ | m-OCH₃ | o-OH | H | CH₃ |
| (411) | OCH₃ | m-OCH₃ | m-OH | H | CH₃ |
| (412) | OCH₃ | m-OCH₃ | p-OH | H | CH₃ |
| (413) | OCH₃ | m-OCH₃ | o-OH | o-Cl | CH₃ |
| (414) | OCH₃ | m-OCH₃ | m-OH | o-Cl | CH₃ |
| (415) | OCH₃ | m-OCH₃ | p-OH | o-Cl | CH₃ |
| (416) | OCH₃ | m-OCH₃ | m-OH | m-Cl | CH₃ |
| (417) | OCH₃ | m-OCH₃ | p-OH | m-Cl | CH₃ |
| (418) | OCH₃ | m-OCH₃ | o-OH | o-F | CH₃ |
| (419) | OCH₃ | m-OCH₃ | m-OH | o-F | CH₃ |
| (420) | OCH₃ | m-OCH₃ | p-OH | o-F | CH₃ |
| (421) | OCH₃ | m-OCH₃ | o-OH | m-F | CH₃ |
| (422) | OCH₃ | m-OCH₃ | m-OH | m-F | CH₃ |
| (423) | OCH₃ | m-OCH₃ | p-OH | m-F | CH₃ |
| (424) | OCH₃ | m-OCH₃ | o-OH | p-F | CH₃ |
| (425) | OCH₃ | m-OCH₃ | m-OH | p-F | CH₃ |
| (426) | OCH₃ | m-OCH₃ | o-OH | o-OH | CH₃ |
| (427) | OCH₃ | m-OCH₃ | m-OH | o-OH | CH₃ |
| (428) | OCH₃ | m-OCH₃ | p-OH | o-OH | CH₃ |
| (429) | OCH₃ | m-OCH₃ | m-OH | m-OH | CH₃ |
| (430) | OCH₃ | m-OCH₃ | p-OH | m-OH | CH₃ |
| (431) | OCH₃ | m-OCH₃ | o-CH₃ | H | CH₃ |
| (432) | OCH₃ | m-OCH₃ | m-CH₃ | H | CH₃ |
| (433) | OCH₃ | m-OCH₃ | p-CH₃ | H | CH₃ |
| (434) | OCH₃ | m-OCH₃ | o-CH₃ | o-Cl | CH₃ |
| (435) | OCH₃ | m-OCH₃ | m-CH₃ | o-Cl | CH₃ |
| (436) | OCH₃ | m-OCH₃ | p-CH₃ | o-Cl | CH₃ |
| (437) | OCH₃ | m-OCH₃ | m-CH₃ | m-Cl | CH₃ |
| (438) | OCH₃ | m-OCH₃ | p-CH₃ | m-Cl | CH₃ |
| (439) | OCH₃ | m-OCH₃ | o-CH₃ | o-F | CH₃ |
| (440) | OCH₃ | m-OCH₃ | m-CH₃ | o-F | CH₃ |
| (441) | OCH₃ | m-OCH₃ | p-CH₃ | o-F | CH₃ |
| (442) | OCH₃ | m-OCH₃ | o-CH₃ | m-F | CH₃ |
| (443) | OCH₃ | m-OCH₃ | m-CH₃ | m-F | CH₃ |
| (444) | OCH₃ | m-OCH₃ | p-CH₃ | m-F | CH₃ |
| (445) | OCH₃ | m-OCH₃ | o-CH₃ | p-F | CH₃ |
| (446) | OCH₃ | m-OCH₃ | m-CH₃ | p-F | CH₃ |
| (447) | OCH₃ | m-OCH₃ | o-CH₃ | o-CH₃ | CH₃ |
| (448) | OCH₃ | m-OCH₃ | m-CH₃ | o-CH₃ | CH₃ |
| (449) | OCH₃ | m-OCH₃ | p-CH₃ | o-CH₃ | CH₃ |
| (450) | OCH₃ | m-OCH₃ | m-CH₃ | m-CH₃ | CH₃ |
| (451) | OCH₃ | m-OCH₃ | p-CH₃ | m-CH₃ | CH₃ |
| (452) | OCH₃ | H | H | H | CH₃ |

-continued

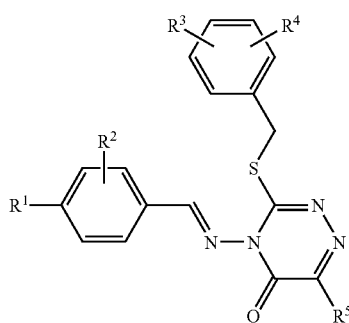

Ia

| | R¹ | R² | R³ | R⁴ | R⁵ |
|---|---|---|---|---|---|
| (453) | OCH₃ | H | o-Cl | H | CH₃ |
| (454) | OCH₃ | H | m-Cl | H | CH₃ |
| (455) | OCH₃ | H | p-Cl | H | CH₃ |
| (456) | OCH₃ | H | o-Cl | o-Cl | CH₃ |
| (457) | OCH₃ | H | m-Cl | o-Cl | CH₃ |
| (458) | OCH₃ | H | p-Cl | o-Cl | CH₃ |
| (459) | OCH₃ | H | m-Cl | m-Cl | CH₃ |
| (460) | OCH₃ | H | p-Cl | m-Cl | CH₃ |
| (461) | OCH₃ | H | o-Cl | o-F | CH₃ |
| (462) | OCH₃ | H | m-Cl | o-F | CH₃ |
| (463) | OCH₃ | H | p-Cl | o-F | CH₃ |
| (464) | OCH₃ | H | o-Cl | m-F | CH₃ |
| (465) | OCH₃ | H | m-Cl | m-F | CH₃ |
| (466) | OCH₃ | H | p-Cl | m-F | CH₃ |
| (467) | OCH₃ | H | o-Cl | p-F | CH₃ |
| (468) | OCH₃ | H | m-Cl | p-F | CH₃ |
| (469) | OCH₃ | H | o-F | o-F | CH₃ |
| (470) | OCH₃ | H | m-F | o-F | CH₃ |
| (471) | OCH₃ | H | p-F | o-F | CH₃ |
| (472) | OCH₃ | H | m-F | m-F | CH₃ |
| (473) | OCH₃ | H | p-F | m-F | CH₃ |
| (474) | OCH₃ | H | o-OCH₃ | H | CH₃ |
| (475) | OCH₃ | H | m-OCH₃ | H | CH₃ |
| (476) | OCH₃ | H | p-OCH₃ | H | CH₃ |
| (477) | OCH₃ | H | o-OCH₃ | o-Cl | CH₃ |
| (478) | OCH₃ | H | m-OCH₃ | o-Cl | CH₃ |
| (479) | OCH₃ | H | p-OCH₃ | o-Cl | CH₃ |
| (480) | OCH₃ | H | m-OCH₃ | m-Cl | CH₃ |
| (481) | OCH₃ | H | p-OCH₃ | m-Cl | CH₃ |
| (482) | OCH₃ | H | o-OCH₃ | o-F | CH₃ |
| (483) | OCH₃ | H | m-OCH₃ | o-F | CH₃ |
| (484) | OCH₃ | H | p-OCH₃ | o-F | CH₃ |
| (485) | OCH₃ | H | o-OCH₃ | m-F | CH₃ |
| (486) | OCH₃ | H | m-OCH₃ | m-F | CH₃ |
| (487) | OCH₃ | H | p-OCH₃ | m-F | CH₃ |
| (488) | OCH₃ | H | o-OCH₃ | p-F | CH₃ |
| (489) | OCH₃ | H | m-OCH₃ | p-F | CH₃ |
| (490) | OCH₃ | H | o-OCH₃ | o-OCH₃ | CH₃ |
| (491) | OCH₃ | H | m-OCH₃ | o-OCH₃ | CH₃ |
| (492) | OCH₃ | H | p-OCH₃ | o-OCH₃ | CH₃ |
| (493) | OCH₃ | H | m-OCH₃ | m-OCH₃ | CH₃ |
| (494) | OCH₃ | H | p-OCH₃ | m-OCH₃ | CH₃ |
| (495) | OCH₃ | H | o-OH | H | CH₃ |
| (496) | OCH₃ | H | m-OH | H | CH₃ |
| (497) | OCH₃ | H | p-OH | H | CH₃ |
| (498) | OCH₃ | H | o-OH | o-Cl | CH₃ |
| (499) | OCH₃ | H | m-OH | o-Cl | CH₃ |
| (500) | OCH₃ | H | p-OH | o-Cl | CH₃ |
| (501) | OCH₃ | H | m-OH | m-Cl | CH₃ |
| (502) | OCH₃ | H | p-OH | m-Cl | CH₃ |
| (503) | OCH₃ | H | o-OH | o-F | CH₃ |
| (504) | OCH₃ | H | m-OH | o-F | CH₃ |
| (505) | OCH₃ | H | p-OH | o-F | CH₃ |
| (506) | OCH₃ | H | o-OH | m-F | CH₃ |
| (507) | OCH₃ | H | m-OH | m-F | CH₃ |
| (508) | OCH₃ | H | p-OH | m-F | CH₃ |
| (509) | OCH₃ | H | o-OH | p-F | CH₃ |
| (510) | OCH₃ | H | m-OH | p-F | CH₃ |
| (511) | OCH₃ | H | o-OH | o-OH | CH₃ |
| (512) | OCH₃ | H | m-OH | o-OH | CH₃ |

-continued

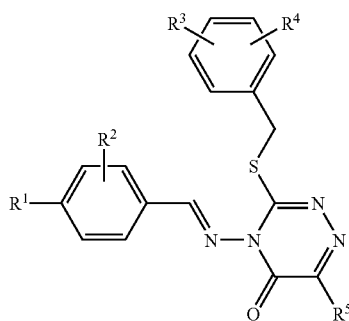

Ia

| | R¹ | R² | R³ | R⁴ | R⁵ |
|---|---|---|---|---|---|
| (513) | OCH₃ | H | p-OH | o-OH | CH₃ |
| (514) | OCH₃ | H | m-OH | m-OH | CH₃ |
| (515) | OCH₃ | H | p-OH | m-OH | CH₃ |
| (516) | OCH₃ | H | o-CH₃ | H | CH₃ |
| (517) | OCH₃ | H | m-CH₃ | H | CH₃ |
| (518) | OCH₃ | H | p-CH₃ | H | CH₃ |
| (519) | OCH₃ | H | o-CH₃ | o-Cl | CH₃ |
| (520) | OCH₃ | H | m-CH₃ | o-Cl | CH₃ |
| (521) | OCH₃ | H | p-CH₃ | o-Cl | CH₃ |
| (522) | OCH₃ | H | m-CH₃ | m-Cl | CH₃ |
| (523) | OCH₃ | H | p-CH₃ | m-Cl | CH₃ |
| (524) | OCH₃ | H | o-CH₃ | o-F | CH₃ |
| (525) | OCH₃ | H | m-CH₃ | o-F | CH₃ |
| (526) | OCH₃ | H | p-CH₃ | o-F | CH₃ |
| (527) | OCH₃ | H | o-CH₃ | m-F | CH₃ |
| (528) | OCH₃ | H | m-CH₃ | m-F | CH₃ |
| (529) | OCH₃ | H | p-CH₃ | m-F | CH₃ |
| (530) | OCH₃ | H | o-CH₃ | p-F | CH₃ |
| (531) | OCH₃ | H | m-CH₃ | p-F | CH₃ |
| (532) | OCH₃ | H | o-CH₃ | o-CH₃ | CH₃ |
| (533) | OCH₃ | H | m-CH₃ | o-CH₃ | CH₃ |
| (534) | OCH₃ | H | p-CH₃ | o-CH₃ | CH₃ |
| (535) | OCH₃ | H | m-CH₃ | m-CH₃ | CH₃ |
| (536) | OCH₃ | H | p-CH₃ | m-CH₃ | CH₃ |
| (537) | OCH₃ | o-Cl | H | H | CH₃ |
| (538) | OCH₃ | o-Cl | o-Cl | H | CH₃ |
| (539) | OCH₃ | o-Cl | m-Cl | H | CH₃ |
| (540) | OCH₃ | o-Cl | p-Cl | H | CH₃ |
| (541) | OCH₃ | o-Cl | o-Cl | o-Cl | CH₃ |
| (542) | OCH₃ | o-Cl | m-Cl | o-Cl | CH₃ |
| (543) | OCH₃ | o-Cl | p-Cl | o-Cl | CH₃ |
| (544) | OCH₃ | o-Cl | m-Cl | m-Cl | CH₃ |
| (545) | OCH₃ | o-Cl | p-Cl | m-Cl | CH₃ |
| (546) | OCH₃ | o-Cl | o-Cl | o-F | CH₃ |
| (547) | OCH₃ | o-Cl | m-Cl | o-F | CH₃ |
| (548) | OCH₃ | o-Cl | p-Cl | o-F | CH₃ |
| (549) | OCH₃ | o-Cl | o-Cl | m-F | CH₃ |
| (550) | OCH₃ | o-Cl | m-Cl | m-F | CH₃ |
| (551) | OCH₃ | o-Cl | p-Cl | m-F | CH₃ |
| (552) | OCH₃ | o-Cl | o-Cl | p-F | CH₃ |
| (553) | OCH₃ | o-Cl | m-Cl | p-F | CH₃ |
| (554) | OCH₃ | o-Cl | o-F | o-F | CH₃ |
| (555) | OCH₃ | o-Cl | m-F | o-F | CH₃ |
| (556) | OCH₃ | o-Cl | p-F | o-F | CH₃ |
| (557) | OCH₃ | o-Cl | m-F | m-F | CH₃ |
| (558) | OCH₃ | o-Cl | p-F | m-F | CH₃ |
| (559) | OCH₃ | o-Cl | o-OCH₃ | H | CH₃ |
| (560) | OCH₃ | o-Cl | m-OCH₃ | H | CH₃ |
| (561) | OCH₃ | o-Cl | p-OCH₃ | H | CH₃ |
| (562) | OCH₃ | o-Cl | o-OCH₃ | o-Cl | CH₃ |
| (563) | OCH₃ | o-Cl | m-OCH₃ | o-Cl | CH₃ |
| (564) | OCH₃ | o-Cl | p-OCH₃ | o-Cl | CH₃ |
| (565) | OCH₃ | o-Cl | m-OCH₃ | m-Cl | CH₃ |
| (566) | OCH₃ | o-Cl | p-OCH₃ | m-Cl | CH₃ |
| (567) | OCH₃ | o-Cl | o-OCH₃ | o-F | CH₃ |
| (568) | OCH₃ | o-Cl | m-OCH₃ | o-F | CH₃ |
| (569) | OCH₃ | o-Cl | p-OCH₃ | o-F | CH₃ |
| (570) | OCH₃ | o-Cl | o-OCH₃ | m-F | CH₃ |
| (571) | OCH₃ | o-Cl | m-OCH₃ | m-F | CH₃ |
| (572) | OCH₃ | o-Cl | p-OCH₃ | m-F | CH₃ |

-continued

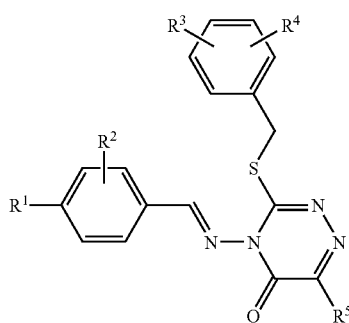

Ia

| | R¹ | R² | R³ | R⁴ | R⁵ |
|---|---|---|---|---|---|
| (573) | OCH₃ | o-Cl | o-OCH₃ | p-F | CH₃ |
| (574) | OCH₃ | o-Cl | m-OCH₃ | p-F | CH₃ |
| (575) | OCH₃ | o-Cl | o-OCH₃ | o-OCH₃ | CH₃ |
| (576) | OCH₃ | o-Cl | m-OCH₃ | o-OCH₃ | CH₃ |
| (577) | OCH₃ | o-Cl | p-OCH₃ | o-OCH₃ | CH₃ |
| (578) | OCH₃ | o-Cl | m-OCH₃ | m-OCH₃ | CH₃ |
| (579) | OCH₃ | o-Cl | p-OCH₃ | m-OCH₃ | CH₃ |
| (580) | OCH₃ | o-Cl | o-OH | H | CH₃ |
| (581) | OCH₃ | o-Cl | m-OH | H | CH₃ |
| (582) | OCH₃ | o-Cl | p-OH | H | CH₃ |
| (583) | OCH₃ | o-Cl | o-OH | o-Cl | CH₃ |
| (584) | OCH₃ | o-Cl | m-OH | o-Cl | CH₃ |
| (585) | OCH₃ | o-Cl | p-OH | o-Cl | CH₃ |
| (586) | OCH₃ | o-Cl | m-OH | m-Cl | CH₃ |
| (587) | OCH₃ | o-Cl | p-OH | m-Cl | CH₃ |
| (588) | OCH₃ | o-Cl | o-OH | o-F | CH₃ |
| (589) | OCH₃ | o-Cl | m-OH | o-F | CH₃ |
| (590) | OCH₃ | o-Cl | p-OH | o-F | CH₃ |
| (591) | OCH₃ | o-Cl | o-OH | m-F | CH₃ |
| (592) | OCH₃ | o-Cl | m-OH | m-F | CH₃ |
| (593) | OCH₃ | o-Cl | p-OH | m-F | CH₃ |
| (594) | OCH₃ | o-Cl | o-OH | p-F | CH₃ |
| (595) | OCH₃ | o-Cl | m-OH | p-F | CH₃ |
| (596) | OCH₃ | o-Cl | o-OH | o-OH | CH₃ |
| (597) | OCH₃ | o-Cl | m-OH | o-OH | CH₃ |
| (598) | OCH₃ | o-Cl | p-OH | o-OH | CH₃ |
| (599) | OCH₃ | o-Cl | m-OH | m-OH | CH₃ |
| (600) | OCH₃ | o-Cl | p-OH | m-OH | CH₃ |
| (601) | OCH₃ | o-Cl | o-CH₃ | H | CH₃ |
| (602) | OCH₃ | o-Cl | m-CH₃ | H | CH₃ |
| (603) | OCH₃ | o-Cl | p-CH₃ | H | CH₃ |
| (604) | OCH₃ | o-Cl | o-CH₃ | o-Cl | CH₃ |
| (605) | OCH₃ | o-Cl | m-CH₃ | o-Cl | CH₃ |
| (606) | OCH₃ | o-Cl | p-CH₃ | o-Cl | CH₃ |
| (607) | OCH₃ | o-Cl | m-CH₃ | m-Cl | CH₃ |
| (608) | OCH₃ | o-Cl | p-CH₃ | m-Cl | CH₃ |
| (609) | OCH₃ | o-Cl | o-CH₃ | o-F | CH₃ |
| (610) | OCH₃ | o-Cl | m-CH₃ | o-F | CH₃ |
| (611) | OCH₃ | o-Cl | p-CH₃ | o-F | CH₃ |
| (612) | OCH₃ | o-Cl | o-CH₃ | m-F | CH₃ |
| (613) | OCH₃ | o-Cl | m-CH₃ | m-F | CH₃ |
| (614) | OCH₃ | o-Cl | p-CH₃ | m-F | CH₃ |
| (615) | OCH₃ | o-Cl | o-CH₃ | p-F | CH₃ |
| (616) | OCH₃ | o-Cl | m-CH₃ | p-F | CH₃ |
| (617) | OCH₃ | o-Cl | o-CH₃ | o-CH₃ | CH₃ |
| (618) | OCH₃ | o-Cl | m-CH₃ | o-CH₃ | CH₃ |
| (619) | OCH₃ | o-Cl | p-CH₃ | o-CH₃ | CH₃ |
| (620) | OCH₃ | o-Cl | m-CH₃ | m-CH₃ | CH₃ |
| (621) | OCH₃ | o-Cl | p-CH₃ | m-CH₃ | CH₃ |
| (622) | OCH₃ | m-OC₂H₅ | H | H | C₂H₅ |
| (623) | OCH₃ | m-OC₂H₅ | o-Cl | H | C₂H₅ |
| (624) | OCH₃ | m-OC₂H₅ | m-Cl | H | C₂H₅ |
| (625) | OCH₃ | m-OC₂H₅ | p-Cl | H | C₂H₅ |
| (626) | OCH₃ | m-OC₂H₅ | o-Cl | o-Cl | C₂H₅ |
| (627) | OCH₃ | m-OC₂H₅ | m-Cl | o-Cl | C₂H₅ |
| (628) | OCH₃ | m-OC₂H₅ | p-Cl | o-Cl | C₂H₅ |
| (629) | OCH₃ | m-OC₂H₅ | m-Cl | m-Cl | C₂H₅ |
| (630) | OCH₃ | m-OC₂H₅ | p-Cl | m-Cl | C₂H₅ |
| (631) | OCH₃ | m-OC₂H₅ | o-Cl | o-F | C₂H₅ |
| (632) | OCH₃ | m-OC₂H₅ | m-Cl | o-F | C₂H₅ |

-continued

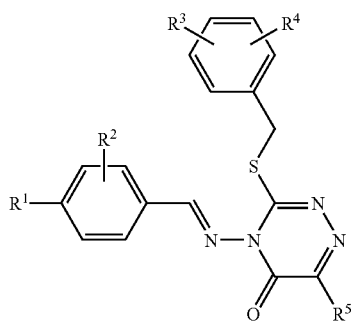

Ia

| | R¹ | R² | R³ | R⁴ | R⁵ | |
|---|---|---|---|---|---|---|
| (633) | OCH₃ | m-OC₂H₅ | p-Cl | o-F | C₂H₅ | |
| (634) | OCH₃ | m-OC₂H₅ | o-Cl | m-F | C₂H₅ | |
| (635) | OCH₃ | m-OC₂H₅ | m-Cl | m-F | C₂H₅ | |
| (636) | OCH₃ | m-OC₂H₅ | p-Cl | m-F | C₂H₅ | |
| (637) | OCH₃ | m-OC₂H₅ | o-Cl | p-F | C₂H₅ | |
| (638) | OCH₃ | m-OC₂H₅ | m-Cl | p-F | C₂H₅ | |
| (639) | OCH₃ | m-OC₂H₅ | o-F | o-F | C₂H₅ | |
| (640) | OCH₃ | m-OC₂H₅ | m-F | o-F | C₂H₅ | |
| (641) | OCH₃ | m-OC₂H₅ | p-F | o-F | C₂H₅ | |
| (642) | OCH₃ | m-OC₂H₅ | m-F | m-F | C₂H₅ | |
| (643) | OCH₃ | m-OC₂H₅ | p-F | m-F | C₂H₅ | |
| (644) | OCH₃ | m-OC₂H₅ | o-OCH₃ | H | C₂H₅ | |
| (645) | OCH₃ | m-OC₂H₅ | m-OCH₃ | H | C₂H₅ | |
| (646) | OCH₃ | m-OC₂H₅ | p-OCH₃ | H | C₂H₅ | |
| (647) | OCH₃ | m-OC₂H₅ | o-OCH₃ | o-Cl | C₂H₅ | |
| (648) | OCH₃ | m-OC₂H₅ | m-OCH₃ | o-Cl | C₂H₅ | |
| (649) | OCH₃ | m-OC₂H₅ | p-OCH₃ | o-Cl | C₂H₅ | |
| (650) | OCH₃ | m-OC₂H₅ | m-OCH₃ | m-Cl | C₂H₅ | |
| (651) | OCH₃ | m-OC₂H₅ | p-OCH₃ | m-Cl | C₂H₅ | |
| (652) | OCH₃ | m-OC₂H₅ | o-OCH₃ | o-F | C₂H₅ | |
| (653) | OCH₃ | m-OC₂H₅ | m-OCH₃ | o-F | C₂H₅ | |
| (654) | OCH₃ | m-OC₂H₅ | p-OCH₃ | o-F | C₂H₅ | |
| (655) | OCH₃ | m-OC₂H₅ | o-OCH₃ | m-F | C₂H₅ | |
| (656) | OCH₃ | m-OC₂H₅ | m-OCH₃ | m-F | C₂H₅ | |
| (657) | OCH₃ | m-OC₂H₅ | H | H | H | |
| (658) | OCH₃ | m-OC₂H₅ | o-Cl | H | H | |
| (659) | OCH₃ | m-OC₂H₅ | m-Cl | H | H | |
| (660) | OCH₃ | m-OC₂H₅ | p-Cl | H | H | |
| (661) | OCH₃ | m-OC₂H₅ | o-Cl | o-Cl | H | |
| (662) | OCH₃ | m-OC₂H₅ | m-Cl | o-Cl | H | |
| (663) | OCH₃ | m-OC₂H₅ | p-Cl | o-Cl | H | |
| (664) | OCH₃ | m-OC₂H₅ | m-Cl | m-Cl | H | |
| (665) | OCH₃ | m-OC₂H₅ | p-Cl | m-Cl | H | |
| (666) | OCH₃ | m-OC₂H₅ | o-Cl | o-F | H | |
| (667) | OCH₃ | m-OC₂H₅ | m-Cl | o-F | H | |
| (668) | OCH₃ | m-OC₂H₅ | p-Cl | o-F | H | |
| (669) | OCH₃ | cyclopentyl-O | H | H | CH₃ | |
| (670) | OCH₃ | cyclopentyl-O | o-Cl | H | CH₃ | |
| (671) | OCH₃ | cyclopentyl-O | m-Cl | H | CH₃ | |
| (672) | OCH₃ | cyclopentyl-O | p-Cl | H | CH₃ | |
| (673) | OCH₃ | cyclopentyl-O | o-F | H | CH₃ | (m.p. 155° C.) |

-continued
Ia
| | R¹ | R² | R³ | R⁴ | R⁵ | |
|---|---|---|---|---|---|---|
| (674) | OCH₃ | O | m-F | H | CH₃ | |
| (675) | OCH₃ | O | p-F | H | CH₃ | |
| (676) | OCH₃ | O | o-Cl | o-Cl | CH₃ | |
| (677) | OCH₃ | O | m-Cl | o-Cl | CH₃ | |
| (678) | OCH₃ | O | p-Cl | o-Cl | CH₃ | |
| (679) | OCH₃ | O | m-Cl | m-Cl | CH₃ | |
| (680) | OCH₃ | O | p-Cl | m-Cl | CH₃ | |
| (681) | OCH₃ | O | o-Cl | o-F | CH₃ | (m.p. 180° C.) |
| (682) | OCH₃ | O | m-Cl | o-F | CH₃ | |
| (683) | OCH₃ | O | p-Cl | o-F | CH₃ | |
| (684) | OCH₃ | O | o-Cl | m-F | CH₃ | |
| (685) | OCH₃ | O | m-Cl | m-F | CH₃ | |

-continued

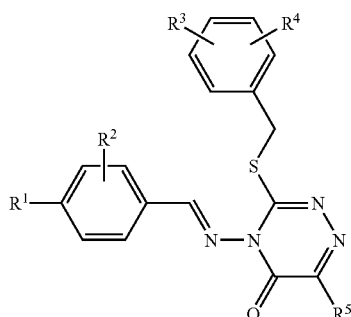

Ia

| | R¹ | R² | R³ | R⁴ | R⁵ |
|---|---|---|---|---|---|
| (686) | OCH₃ | cyclopentyl-O | p-Cl | m-F | CH₃ |
| (687) | OCH₃ | cyclopentyl-O | o-Cl | p-F | CH₃ |
| (688) | OCH₃ | cyclopentyl-O | m-Cl | p-F | CH₃ |
| (689) | OCH₃ | cyclopentyl-O | o-F | o-F | CH₃ |
| (690) | OCH₃ | cyclopentyl-O | m-F | o-F | CH₃ |
| (691) | OCH₃ | cyclopentyl-O | p-F | o-F | CH₃ |
| (692) | OCH₃ | cyclopentyl-O | m-F | m-F | CH₃ |
| (693) | OCH₃ | cyclopentyl-O | p-F | m-F | CH₃ |
| (694) | OCH₃ | cyclopentyl-O | o-OCH₃ | H | CH₃ |
| (695) | OCH₃ | cyclopentyl-O | m-OCH₃ | H | CH₃ |
| (696) | OCH₃ | cyclopentyl-O | p-OCH₃ | H | CH₃ |
| (697) | OCH₃ | cyclopentyl-O | o-OCH₃ | o-Cl | CH₃ |

-continued

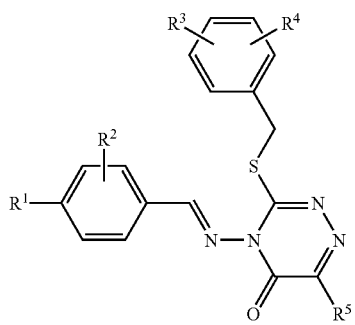

Ia

| | R¹ | R² | R³ | R⁴ | R⁵ |
|---|---|---|---|---|---|
| (698) | OCH₃ | cyclopentyl-O | m-OCH₃ | o-Cl | CH₃ |
| (699) | OCH₃ | cyclopentyl-O | p-OCH₃ | o-Cl | CH₃ |
| (700) | OCH₃ | cyclopentyl-O | m-OCH₃ | m-Cl | CH₃ |
| (701) | OCH₃ | cyclopentyl-O | p-OCH₃ | m-Cl | CH₃ |
| (702) | OCH₃ | cyclopentyl-O | o-OCH₃ | o-F | CH₃ |
| (703) | OCH₃ | cyclopentyl-O | m-OCH₃ | o-F | CH₃ |
| (704) | OCH₃ | cyclopentyl-O | p-OCH₃ | o-F | CH₃ |
| (705) | OCH₃ | cyclopentyl-O | o-OCH₃ | m-F | CH₃ |
| (706) | OCH₃ | cyclopentyl-O | m-OCH₃ | m-F | CH₃ |
| (707) | OCH₃ | cyclopentyl-O | p-OCH₃ | m-F | CH₃ |
| (708) | OCH₃ | cyclopentyl-O | o-OCH₃ | p-F | CH₃ |
| (709) | OCH₃ | cyclopentyl-O | m-OCH₃ | p-F | CH₃ |

-continued
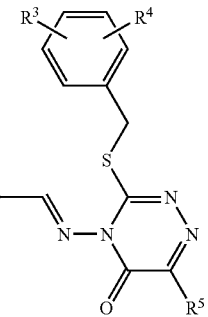
Ia
| | R¹ | R² | R³ | R⁴ | R⁵ |
|---|---|---|---|---|---|
| (710) | OCH₃ | O | o-OCH₃ | o-OCH₃ | CH₃ |
| (711) | OCH₃ | O | m-OCH₃ | o-OCH₃ | CH₃ |
| (712) | OCH₃ | O | p-OCH₃ | o-OCH₃ | CH₃ |
| (713) | OCH₃ | O | m-OCH₃ | m-OCH₃ | CH₃ |
| (714) | OCH₃ | O | p-OCH₃ | m-OCH₃ | CH₃ |
| (715) | OCH₃ | O | o-OH | H | CH₃ |
| (716) | OCH₃ | O | m-OH | H | CH₃ |
| (717) | OCH₃ | O | p-OH | H | CH₃ |
| (718) | OCH₃ | O | o-OH | o-Cl | CH₃ |
| (719) | OCH₃ | O | m-OH | o-Cl | CH₃ |
| (720) | OCH₃ | O | p-OH | o-Cl | CH₃ |
| (721) | OCH₃ | O | m-OH | m-Cl | CH₃ |

-continued

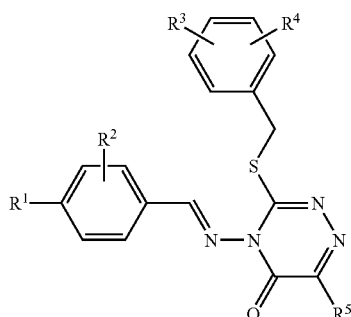

Ia

| | R¹ | R² | R³ | R⁴ | R⁵ |
|---|---|---|---|---|---|
| (722) | OCH₃ | cyclopentyl-O | p-OH | m-Cl | CH₃ |
| (723) | OCH₃ | cyclopentyl-O | o-OH | o-F | CH₃ |
| (724) | OCH₃ | cyclopentyl-O | m-OH | o-F | CH₃ |
| (725) | OCH₃ | cyclopentyl-O | p-OH | o-F | CH₃ |
| (726) | OCH₃ | cyclopentyl-O | o-OH | m-F | CH₃ |
| (727) | OCH₃ | cyclopentyl-O | m-OH | m-F | CH₃ |
| (728) | OCH₃ | cyclopentyl-O | p-OH | m-F | CH₃ |
| (729) | OCH₃ | cyclopentyl-O | o-OH | p-F | CH₃ |
| (730) | OCH₃ | cyclopentyl-O | m-OH | p-F | CH₃ |
| (731) | OCH₃ | cyclopentyl-O | o-OH | o-OH | CH₃ |
| (732) | OCH₃ | cyclopentyl-O | m-OH | o-OH | CH₃ |
| (733) | OCH₃ | cyclopentyl-O | p-OH | o-OH | CH₃ |

-continued

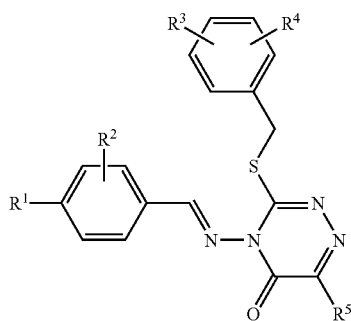

Ia

| | R¹ | R² | R³ | R⁴ | R⁵ |
|---|---|---|---|---|---|
| (734) | OCH₃ | cyclopentyl-O | m-OH | m-OH | CH₃ |
| (735) | OCH₃ | cyclopentyl-O | p-OH | m-OH | CH₃ |
| (736) | OCH₃ | cyclopentyl-O | o-CH₃ | H | CH₃ |
| (737) | OCH₃ | cyclopentyl-O | m-CH₃ | H | CH₃ |
| (738) | OCH₃ | cyclopentyl-O | p-CH₃ | H | CH₃ |
| (739) | OCH₃ | cyclopentyl-O | o-CH₃ | o-Cl | CH₃ |
| (740) | OCH₃ | cyclopentyl-O | m-CH₃ | o-Cl | CH₃ |
| (741) | OCH₃ | cyclopentyl-O | p-CH₃ | o-Cl | CH₃ |
| (742) | OCH₃ | cyclopentyl-O | m-CH₃ | m-Cl | CH₃ |
| (743) | OCH₃ | cyclopentyl-O | p-CH₃ | m-Cl | CH₃ |
| (744) | OCH₃ | cyclopentyl-O | o-CH₃ | o-F | CH₃ |
| (745) | OCH₃ | cyclopentyl-O | m-CH₃ | o-F | CH₃ |

-continued

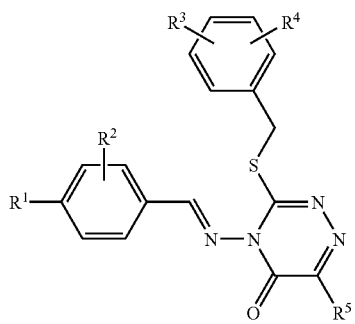

Ia

| | R¹ | R² | R³ | R⁴ | R⁵ |
|---|---|---|---|---|---|
| (746) | OCH₃ | cyclopentyl-O | p-CH₃ | o-F | CH₃ |
| (747) | OCH₃ | cyclopentyl-O | o-CH₃ | m-F | CH₃ |
| (748) | OCH₃ | cyclopentyl-O | m-CH₃ | m-F | CH₃ |
| (749) | OCH₃ | cyclopentyl-O | p-CH₃ | m-F | CH₃ |
| (750) | OCH₃ | cyclopentyl-O | o-CH₃ | p-F | CH₃ |
| (751) | OCH₃ | cyclopentyl-O | m-CH₃ | p-F | CH₃ |
| (752) | OCH₃ | cyclopentyl-O | o-CH₃ | o-CH₃ | CH₃ |
| (753) | OCH₃ | cyclopentyl-O | m-CH₃ | o-CH₃ | CH₃ |
| (754) | OCH₃ | cyclopentyl-O | p-CH₃ | o-CH₃ | CH₃ |
| (755) | OCH₃ | cyclopentyl-O | m-CH₃ | m-CH₃ | CH₃ |
| (756) | OCH₃ | cyclopentyl-O | p-CH₃ | m-CH₃ | CH₃ |

The following compounds of the formula Ib are obtained analogously using the corresponding starting compounds:

| | $R^1$ | $R^2$ | $R^3$ | $R^4$ | $R^5$ | |
|---|---|---|---|---|---|---|
| (757) | OCH₃ | m-OC₂H₅ | H | H | CH₃ | (m.p. 220° C.) |
| (758) | OCH₃ | m-OC₂H₅ | o-Cl | H | CH₃ | |
| (759) | OCH₃ | m-OC₂H₅ | m-Cl | H | CH₃ | |
| (760) | OCH₃ | m-OC₂H₅ | p-Cl | H | CH₃ | |
| (761) | OCH₃ | m-OC₂H₅ | o-F | H | CH₃ | |
| (762) | OCH₃ | m-OC₂H₅ | m-F | H | CH₃ | |
| (763) | OCH₃ | m-OC₂H₅ | p-F | H | CH₃ | |
| (764) | OCH₃ | cyclopentyl-O | H | H | CH₃ | (m.p. 169° C.) |
| (765) | OCH₃ | cyclopentyl-O | o-Cl | H | CH₃ | |
| (766) | OCH₃ | cyclopentyl-O | m-Cl | H | CH₃ | |
| (767) | OCH₃ | cyclopentyl-O | p-Cl | H | CH₃ | |
| (768) | OCH₃ | cyclopentyl-O | o-F | H | CH₃ | |
| (769) | OCH₃ | cyclopentyl-O | m-F | H | CH₃ | |
| (770) | OCH₃ | cyclopentyl-O | p-F | H | CH₃ | |

The following compounds of the formula Ic are obtained analogously using the corresponding starting compounds:

| | $R^1$ | $R^2$ | $R^3$ | $R^4$ | $R^5$ |
|---|---|---|---|---|---|
| (771) | OCH₃ | m-OC₂H₅ | H | H | CH₃ |
| (772) | OCH₃ | m-OC₂H₅ | o-Cl | H | CH₃ |
| (773) | OCH₃ | m-OC₂H₅ | m-Cl | H | CH₃ |
| (774) | OCH₃ | m-OC₂H₅ | o-F | H | CH₃ |
| (775) | OCH₃ | m-OC₂H₅ | m-F | H | CH₃ |

The examples below relate to pharmaceutical preparations:

Example A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of NaH₂PO₄.2H₂O, 28.48 g of Na₂HPO₄.12H₂O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced in a conventional manner into hard gelatine capsules in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with pump mechanism. The solution can be sprayed into the mouth or nose. One spray shot (about 0.1 ml) corresponds to a dose of about 0.14 mg.

The invention claimed is:

1. A compound of formula I

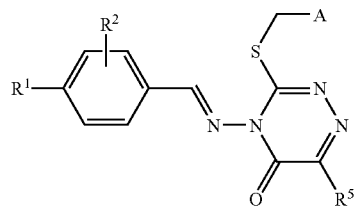

wherein
R$^1$ and R$^2$ are each, independently of one another, H, OH, OR$^6$, SR$^6$, SOR$^6$, SO$_2$R$^6$, Hal or together are alternatively —O—CH$_2$—O—,
A is R$^3$- and R$^4$-substituted phenyl, 2-, 3- or 4-pyridyl, 4- or 5-pyrimidyl, 3- or 4-pyridazyl or 2- or 3-pyrazinyl,
R$^3$ and R$^4$ are each, independently of one another, H, OH, OR$^6$, SR$^6$, SOR$^6$, SO$_2$R$^6$, R$^6$, Hal or together are alternatively —O—CH$_2$—O—,
R$^5$ is H or alkyl having from 1 to 10 carbon atoms,
R$^6$ is alkyl having from 1 to 10 carbon atoms, which may be substituted by from 1 to 5 F and/or Cl atoms, cycloalkyl having 3-7 carbon atoms, alkylenecycloalkyl having 5-10 carbon atoms or alkenyl having 2-8 carbon atoms,
Hal is F, Cl, Br or I,
and physiologically acceptable salts and solvates thereof.

2. The compound of claim 1, wherein R$^5$ is a methyl group.

3. The compound of claim 1, wherein R$^1$ and R$^2$ are each, independently of one another, OR$^6$.

4. The compound of claim 1, wherein R$^6$ is an alkyl group having 1-10 carbon atoms or a cycloalkyl group having 3-7 carbon atoms.

5. The compound of claim 1, wherein A is phenyl, 2-,3- or 4-pyridyl or 4- or 5-pyrimidyl, and R$^3$ and R$^4$ are each, independently of one another, R$^6$, H, Cl, F, CF$_3$ or OR$^6$.

6. The compound of claim 1, which is:
    (a) 4-[(3-ethoxy-4-methoxybenzylidene)amino]-3-(benzylsulfanyl)-6-methyl-4H-1,2,4-triazin-5-one,
    (b) 4-[(3-ethoxy-4-methoxybenzylidene)amino]-3-(2-fluorobenzylsulfanyl)-6-methyl-4H-1,2,4-triazin-5-one,
    (c) 4-[(3-ethoxy-4-methoxybenzylidene)amino]-3-(2-chloro-6-fluorobenzylsulfanyl)-6-methyl-4H-1,2,4-triazin-5-one,
    (d) 4-[(3-ethoxy-4-methoxybenzylidene)amino]-6-methyl-3-(pyridin-3-ylmethylsulfanyl)-4H-1,2,4-triazin-5-one,
    (e) 4-[(3-cyclopentyloxy-4-methoxybenzylidene)amino]-3-(benzylsulfanyl)-6-methyl-4H-1,2,4-triazin-5-one,
    (f) 4-[(3-cyclopentyloxy-4-methoxybenzylidene)amino]-3-(2-fluorobenzylsulfanyl)-6-methyl-4H-1,2,4-triazin-5-one,
    (g) 4-[(3-cyclopentyloxy-4-methoxybenzylidene)amino]-3-(2-chloro-6-fluorobenzylsulfanyl)-6-methyl-4H-1,2,4-triazin-5-one, or
    (h) 4-[(3-cyclopentyloxy-4-methoxybenzylidene)amino]-6-methyl-3-(pyridin-3-ylmethylsulfanyl)-4H-1,2,4-triazin-5-one,
and physiologically acceptable salts and solvates thereof.

7. A process for the preparation of a compound of claim 1 comprising reacting a compound of formula II

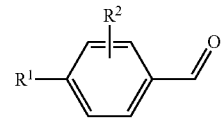

wherein
R$^1$ and R$^2$ are as defined in claim 1,
with a compound of the formula III

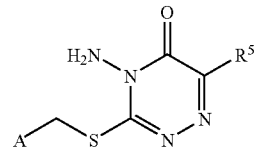

wherein
A and R$^5$ are as defined in claim 1,
and optionally converting a basic compound of formula I into a salt by treatment with an acid.

8. A method of inhibiting phosphodiesterase IV, comprising contacting said phosphodiesterase with a compound of claim 1.

9. A pharmaceutical preparation comprising at least one compound of claim 1 and a pharmaceutically acceptable excipient or adjuvant.

10. A process for the preparation of a pharmaceutical preparation comprising converting at least one compound of claim 1 into a suitable dosage form together with at least one solid, liquid or semi-liquid excipient or adjuvant.

* * * * *

UNITED STATES PATENT AND TRADEMARK OFFICE
CERTIFICATE OF CORRECTION

PATENT NO. : 7,485,639 B2  Page 1 of 1
APPLICATION NO. : 10/484172
DATED : February 3, 2009
INVENTOR(S) : Effenweiler et al.

It is certified that error appears in the above-identified patent and that said Letters Patent is hereby corrected as shown below:

Column 50, line 4, reads "and physiologically acceptable salts and solvents thereof," should read -- or a physiologically acceptable salt or solvent thereof --.

Column 50, line 36, reads "and physiologically acceptable salts and solvents thereof," should read -- or a physiologically acceptable salt or solvent thereof --.

Signed and Sealed this

Thirty-first Day of March, 2009

JOHN DOLL
*Acting Director of the United States Patent and Trademark Office*